(12) United States Patent
Hu et al.

(10) Patent No.: US 8,494,115 B2
(45) Date of Patent: Jul. 23, 2013

(54) METHODS AND APPARATUS FOR HARDWARE BASED RADIATION DOSE CALCULATION

(75) Inventors: Xiaobo Sharon Hu, Granger, IN (US); Cedric Xinsheng Yu, Clarksville, MD (US); Bo Zhou, South Bend, IN (US); Danny Ziyi Chen, Granger, IN (US); Kevin Whitton, Chicago, IL (US)

(73) Assignees: The University of Notre Dame du Lac, Notre Dame, IN (US); The University of Maryland, Baltimore, Baltimore, MD (US)

( * ) Notice: Subject to any disclaimer, the term of this patent is extended or adjusted under 35 U.S.C. 154(b) by 1661 days.

(21) Appl. No.: 11/685,475

(22) Filed: Mar. 13, 2007

(65) Prior Publication Data
US 2013/0158879 A1  Jun. 20, 2013

Related U.S. Application Data

(60) Provisional application No. 60/782,125, filed on Mar. 14, 2006.

(51) Int. Cl.
*A61N 5/10*  (2006.01)

(52) U.S. Cl.
USPC .......................................................... 378/65

(58) Field of Classification Search
USPC .......................................................... 378/65
See application file for complete search history.

(56) References Cited

U.S. PATENT DOCUMENTS

| | | | | |
|---|---|---|---|---|
| 5,317,616 A | * | 5/1994 | Swerdloff et al. | 378/65 |
| 6,301,329 B1 | * | 10/2001 | Surridge | 378/65 |
| 6,546,073 B1 | * | 4/2003 | Lee | 378/65 |
| 6,714,620 B2 | * | 3/2004 | Caflisch et al. | 378/65 |
| 6,792,073 B2 | * | 9/2004 | Deasy et al. | 378/65 |
| 6,882,702 B2 | * | 4/2005 | Luo | 378/65 |
| 7,046,762 B2 | * | 5/2006 | Lee | 378/65 |
| 7,197,404 B2 | * | 3/2007 | Holland | 702/28 |
| 7,519,150 B2 | * | 4/2009 | Romesberg et al. | 378/65 |
| 7,907,697 B2 | * | 3/2011 | Maltz | 378/7 |
| 8,125,813 B2 | * | 2/2012 | Nizin et al. | 365/65 |
| 2004/0096033 A1 | | 5/2004 | Seppi et al. | |
| 2004/0165696 A1 | | 8/2004 | Lee | |
| 2006/0017015 A1 | | 1/2006 | Sliski et al. | |

FOREIGN PATENT DOCUMENTS

WO      2005052721      6/2005

OTHER PUBLICATIONS

Bo Zhou et al., "Memory-Efficient Volume Ray Tracing on GPU for Radiotherapy," 2011 IEEE 9th Symposium on Application Specific Processors (SASP), 46-51.*
Bo Zhou et al., "A Multi-FPGA Accelerator for Radiation Dose Calculation in Cancer Treatment," 2009 IEEE 7th Symposium on Application Specific Processors (SASP), 70-79.*

(Continued)

*Primary Examiner* — Allen C. Ho
(74) *Attorney, Agent, or Firm* — Keith R. Jarosik

(57) ABSTRACT

Disclosed is an example method to calculate radiation dose. The method includes receiving a tissue matrix in which the tissue matrix includes a plurality of voxels. The example method also includes producing a first plurality of transport lines with a direction controller in which each transport line is indicative of a cone of irradiated energy, and calculating at least one radiation dose with at least one deposit engine substantially in parallel with producing a second plurality of transport lines with the direction controller.

53 Claims, 28 Drawing Sheets

OTHER PUBLICATIONS

Anders Ahnesjö and Maria Mania Aspradakis, "Dose calculations for external photon beams in radiotherapy," Phys. Med. Biol. 44, R99-R155 (1999).*

Anders Ahnesjö, "Collapsed cone convolution of radiant energy for photon dose calculation in heterogeneous media," Med. Phys. 16(4), 577-592 (1989).*

Whitton et al., "An FPGA Solution for Radiation Dose Calculation," 14th Annual IEEE Symposium on Field-Programmable Custom Computing Machines (FCCM), Apr. 24, 2006 (10 pages).

Zhou et al., "Hardware Acceleration for 3-D Radiation Dose Calculation," IEEE International Conference on Application-Specific Systems, Architectures and Processors (ASAP), Montreal, Quebec, Canada, Jul. 2007 (9 pages).

International Bureau, International Preliminary Report on Patentability for International application No. PCT/US2007/063891, Sep. 16, 2008, 6 pages.

International Search Report for PCT/US07/63891, 2 pages, Feb. 15, 2008.

Written Opinion of the international Search Authority for PCT/US07/63891, 6 pages, Feb. 15, 2008.

* cited by examiner

1: procedure 1D_CONVOLUTION($T(V,E)$)     ▷ $KERNEL$: An array of elements representing a row in the kernel, $Width$: the number of elements in $KERNEL$ and $element$: the next element to enter the convolver
2:     $Return\_Value = Result[Width - 1] + element * KERNEL[Width]$
3:     for $i = Width - 1$ to $1$ do
4:         $Result[i] = Result[i - 1] + element * KERNEL[i]$
5:     end for
6:     $Result[0] = KERNEL[0] * element$
7:     return $Return\_Value$
8: end procedure

FIG. 15

1: procedure P_D($T_i, \rho_i, \Omega_{mn}, A_m, a_m, \eta_i, \Delta r_i, p\_diff, num\_\eta, sum\_\eta, p\_sum$) ▷ $T_i$: TERMA value, $\rho_i$: mass density, $\Omega_{mn}$: Solid angle, $A_m$ and $a_m$: exponential kernel values, $\eta_i$: electron volume density, $\Delta r_i$: distance traveled in voxel, $prev\_difference$: difference from previous iteration, $num\_\eta$: number of iterations performed, $sum\_\eta$: previous sum of $\eta$ values, $prev\_sum$: previous radiological distance 2:     $temp\_difference = (1 - e^{-a_m(\eta_i * \Delta r_i + p\_sum)})$ 3:     $p\_sum = p\_sum + \eta_i * \Delta r_i$ 4:     $difference = temp\_difference - p\_diff$ 5:     $p\_diff = temp\_difference$ 6:     $sum\_\eta = sum\_\eta + \eta_i$ 7:     $num\_\eta = num\_\eta + 1$ 8:     $R^p_{mn} = \frac{sum\_\eta}{num\_\eta} * T_i * \rho_i * \Omega_{mn} * \frac{A_m}{a_m^2} * difference$ 9:     return $p\_diff, num\_\eta, sum\_\eta, p\_sum, R^p_{mn}$ 10: end procedure

FIG. 19

METHODS AND APPARATUS FOR HARDWARE BASED RADIATION DOSE CALCULATION

CROSS REFERENCE TO RELATED APPLICATION

This application is a non-provisional application claiming priority from U.S. Provisional Application Ser. No. 60/782,125, filed Mar. 14, 2006, entitled "Methods and Apparatus for Hardware Based Radiation Dose Calculation" and incorporated herein by reference in its entirety.

GOVERNMENT INTEREST STATEMENT

This disclosure was made, in part, with United States government support from the National Institutes of Health, grant No. R01 CA92263, and the National Science Foundation, grant No. CCF-0515203. The United States government has certain rights in this invention.

FIELD OF THE DISCLOSURE

The present disclosure relates to the treatment planning step of radiation therapy, and in particular to radiation dose calculation.

BACKGROUND OF RELATED ART

Radiation therapy is a common form of cancer treatment that involves the use of certain types of energy (called ionizing radiation) to kill cancer cells and shrink tumors. There are two main types of radiation therapy, internal radiation (brachytherapy) and external radiation (systemic).

Systemic therapy includes radiation that is delivered from a device external to the patient, and is typically delivered from a linear accelerator, a synchrotron, or a cyclotron, and can be used to treat most types of solid tumors. Typically, external radiation therapy is performed over multiple sessions to maximize the amount of radiation delivered to the tumor and minimize the amount delivered to the surrounding healthy tissue.

The radiation delivered to a patient is called radiation dose or dosage. A radiation dose is measured using a unit called a gray (Gy) and/or centigrays (cGy). Different tissues and organs are capable of withstanding different amounts of dosage and still functioning correctly. For example, the liver can withstand approximately 3,000 cGy, while the kidneys can only withstand approximately 1,800 cGy.

Planning and delivery of radiation therapy typically involves many different team members. Four of these members may include a radiation oncologist, a dosimetrist, a radiation physicist, and a radiation therapist. A radiation oncologist is a doctor who specializes in the treatment of cancer using radiation and typically participates in many steps of the treatment process. The dosimetrist determines the proper radiation dose for the patient. The radiation physicist, who may participate in both the planning and treatment phases, ensures that the equipment delivers the prescribed amount of radiation to the proper location. The radiation therapist, who also typically participates in the planning and treatment phases, delivers the actual treatment.

During a typical planning stage, a patient lies still on a table while the therapist uses an x-ray machine to define the treatment locations (based on patient contours and tumor location(s). A CT (Computed Tomography) device or an MRI (Magnetic Resonance Imaging) device is typically used in this stage to identify the location of the tumor and identify surrounding healthy tissue and organs. During the treatment process, the areas where radiation will be delivered are marked, such as with a temporary or permanent marker, tiny dots, and/or a tattoo. These locations are then defined for future sessions. For some forms of treatment, especially where the patient may be likely to move, molds may be made to ensure that the patient remains motionless.

Once a treatment plan has been devised, it is typically tested to ensure that the radiation delivered by the plan matches the prescribed dosage from the radiation oncology, which is at least one goal of radiation dose calculation. If there is too little dosage delivered to the target site a tumor may persist, and if there is too high a dosage delivered healthy tissue may be harmed.

Dose Calculation

Generally speaking, radiation dose calculation involves computing the amount of energy, released via a photon beam that is deposited within a region of interest within a patient. These areas of interest are typically further broken down into small cubic volume elements referred to as voxels. The size of these voxels changes depending on many different factors, including the calculation algorithm along with size and location of the tumor. The amount of energy deposited in each voxel is typically accumulated and then the final dose may be calculated by dividing the total energy per voxel by the average density of the matter in that voxel. In other words, radiation dose typically depends not only on the amount of energy, but also on the density of the tissue.

The main methods of photon dose deposition are typically via the Compton effect, pair production, and photoelectric effects. All of these refer to the process of a photon interacting with either an electron or the nucleus of an atom.

The photoelectric effect refers to when an incoming photon undergoes a collision with a tightly bound electron. The photon transfers its energy to the electron and ceases to exist. The electron then ionizes particles around it. The probability of the photoelectric effect depends on the initial energy of the photon and the atomic number of the tissue. The probability increases for low energy photons in tissue with a high atomic number.

The Compton effect typically occurs most frequently (of the three methods) in a clinical setting. The Compton effect occurs when a photon collides with a free electron. Both the photon and the electron are scattered. The photon continues on at a slightly different trajectory and with less energy, while the electron begins to ionize. The probability of this effect occurring is inversely proportional to the energy of the photon and is independent of the atomic number of the tissue.

Pair production occurs when a photon interacts with the nucleus of an atom. The photon gives up its energy to the nucleus. This process creates a pair of electrons, one with a positive charge and one with a negative charge. The positive electron (positron) ionizes until combining with a free electron. This then generates two photons, which scatter in opposite directions. The probability of this effect occurring is proportional to the log of the energy of the photon and is also dependent on the atomic number of the tissue.

Radiation dose calculation is an important step in the treatment of patients requiring radiation therapy. It ensures that the physician prescribed dose agrees with the dose delivered to the patient. At least two methods of dose calculation are in use today. One class of algorithms is known as convolution/superposition, and the other is known as Monte Carlo analysis. Monte Carlo methods are typically the most accurate and also the most computationally intensive methods available. These are not usually used in clinical practice due to the computational load they generate. Convolution/superposition methods are slightly less accurate, but can typically be computed in much less time than Monte Carlo methods. While the overall computational power available continues to increase, it may not efficiently facilitate Monte Carlo analysis techniques in a clinically feasible time.

For example, the University of Maryland Medical Center in Baltimore uses two different software packages to compute radiation dose. One such package includes the PINNACLE® system from Philips, and another package includes PROWESS PANTHER® from Prowess, Inc. However, with these software systems it can take anywhere from 5 to 45 minutes to calculate the dosage from a treatment plan. After the calculation phase, the plan may be examined, and if changes are required another calculation is typically performed before the plan can be reviewed again. Additionally, after an MRI is taken of the patient, the tumor and other organs do not remain in a fixed position. A patient's breathing and/or change of posture may cause a corresponding change in the location of the patient's organs and/or tumor. As a result, additional time is consumed by re-calculating dose.

BRIEF DESCRIPTION OF THE DRAWINGS

FIG. 15 illustrates an example algorithm for performing a one-dimensional convolution.

FIG. 19 is an example algorithm for calculating a primary energy distribution.

DETAILED DESCRIPTION

Figure 1:
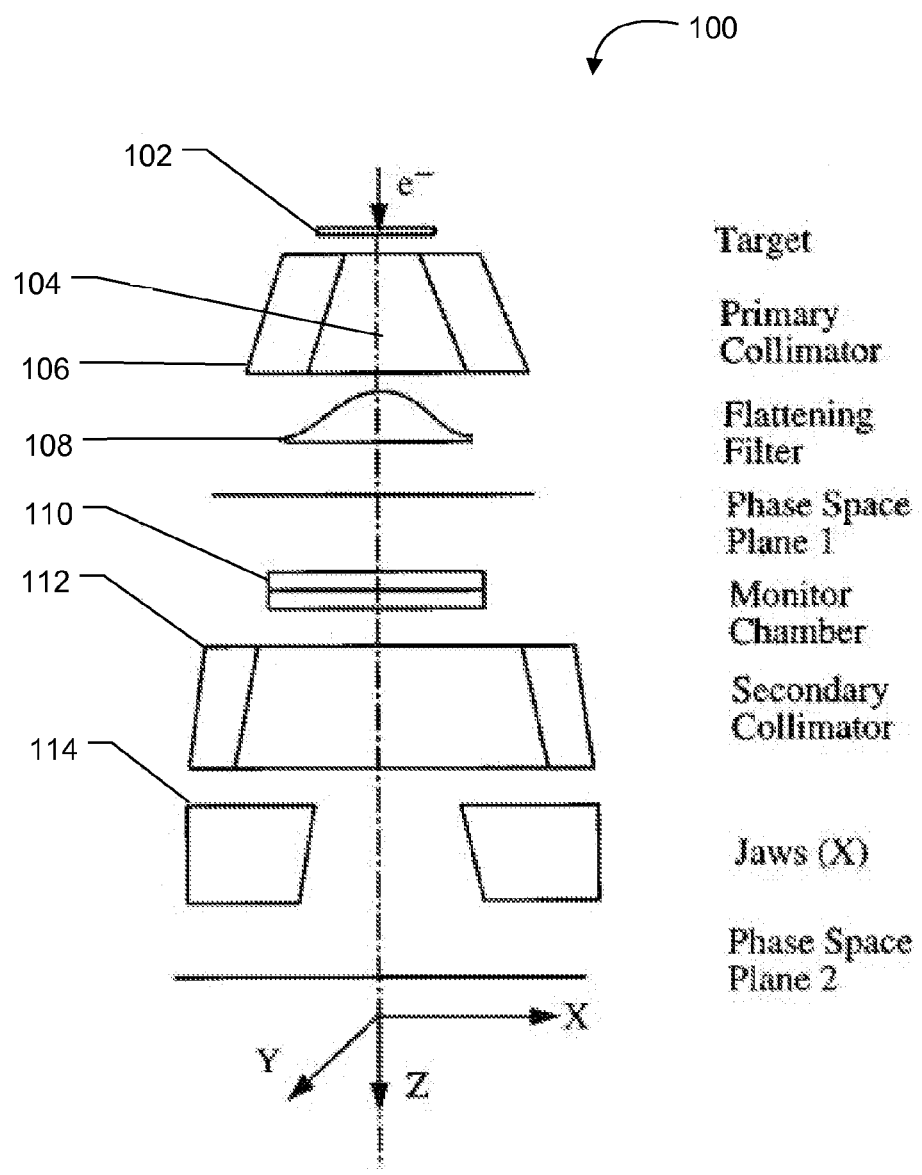
FIG. 1 is an example illustration of a linear accelerator.

The methods and apparatus described herein provide a simple addition to existing host computer and/or processor with moderate cost, but with fewer facilities concerns. Some of the designs presented herein may be implemented as SoPCs (Systems on a Programmable Chip). SoPCs enable rapid prototyping and implementation of new systems. SoPCs typically feature some form of embedded processor (such as the NIOS II® processor from Altera) along with dedicated hardware subsystems. SoPC use has increased in recent years due in part to better software tools, larger FPGA chips, and improvements in embedded and soft-core processors. Many SoPCs have advantages over other solutions due to their programmability, ease of implementation, and lack of additional required hardware.

The methods and apparatus described herein include hardware designs of radiation dose calculation methods. These designs have been shown to outperform existing software dose calculation implementations. They incorporate several different hardware design techniques, including pipelining, double buffering, and ideas from array processing. With one example design, an embedded soft-core processor is utilized, and both designs may access off-chip memory subsystems and/or networked data, without limitation.

Homogeneous and Inhomogeneous Media

Radiation dose calculation may be performed on homogeneous or inhomogeneous media. Homogeneous media means that there is only one type of tissue present in the region of interest. This situation would not typically occur in practice, but certain portions of the body can be assumed to be nearly homogeneous with little loss of accuracy. Inhomogeneous, or heterogeneous media, refers to situations where there are multiple types of tissue present in the region of interest. An example would be a mediastinum (chest region) region of interest. This region may include the lungs, the heart, bone, etc.

If radiation dose calculation can be performed on homogeneous media, then it is typically not necessary to perform inhomogeneity corrections and the use of direct convolution can be applied. As such, a direct convolution implementation (e.g., by using the NIOS® soft-core processor by Altera) that functions on an FPGA (Field Programmable Gate Array) using integer arithmetic is described herein. This convolution may be quicker than a commodity CPU by up to a factor of 35.12 for the convolution of a 100×100×100 matrix with a 100×100×100 kernel and illustrates the effectiveness of using an FPGA over a CPU. This implementation does not actually calculate radiation dose, but instead performs operations similar to those required as an evaluation of the potential speed increase. If the dose calculation must be performed in inhomogeneous media, as is usually the case, direct convolution does not typically yield accurate enough results for clinical practice. For these situations, another dose calculation method is implemented, as described in further detail below.

For inhomogeneous media, a three dimensional convolution/superposition collapse cone algorithm is described herein for an FPGA to achieve performance above that obtainable using a traditional CPU. The dose calculation algorithm described herein makes use of an exponential kernel and the collapse cone approximation for calculating dose, as discussed in further detail below.

Simulations of the designs described herein have shown to outperform a commodity CPU by a factor of 21.6 for a reasonable calculation size. The methods and apparatus described herein assume that both the TERMA (Total Energy per unit MAss) and kernel are provided. The calculation of both the TERMA and kernel require 0.25 seconds on an example computer used for concept verification purposes. With that same computer, the entire calculation requires 61.198 seconds for an 11×11×30 region of interest. Therefore, the portions of the software not placed in a hardware implementation account for only about 0.4% of the calculation time for a decently sized region of interest. Accordingly, approximately 99.6% of the calculation time is spent performing tasks converted to hardware. As described in further detail below, the hardware implementation(s) perform the task of using a collapse cone superposition algorithm to calculate the dose using the available TERMA and kernel.

Results of the dose calculation hardware have been verified against a software dose calculation algorithm provided by the University of Maryland Medical Center. The results of the hardware algorithm are within 1.15% on average of the software algorithm and demonstrate the correct functioning of the hardware implementation.

In general, dose calculation is about determining the amount of energy deposited within a phantom (material used for the absorbing medium in experimental dose measurement) by the photon beam produced by a linear accelerator. The photons in this beam travel to the phantom and then either interact within the phantom, or pass through it. If an interaction occurs within the phantom, energy is released through the collision of photons with other particles. This energy is not all deposited at the site of the interaction, but rather in a type of tear drop shape slanted in the direction of the interacting photon.

To accurately calculate radiation dose, there are many different factors to consider. For example, the source of the radiation is typically considered, and one such machine that delivers radiation is an example linear accelerator 100, as shown in FIG. 1. In the illustrated example of FIG. 1, the linear accelerator is a VARIAN CLINAC 2100C® machine operated in photon mode. FIG. 1 illustrates, in part, electrons hitting the target 102, which produces a photon stream 104. These photons then pass through a primary collimator 106, a flattening filter 108, a monitor chamber 110, a secondary collimator 112, and finally through jaws 114 before they proceed on to a patient.

Once the composition of tissues is known, and the energy (fluence) of the photon beam is known, the distribution of radiant energy released locally in a patient may be calculated. This local distribution is known as the primary energy distribution because the energy is released by the primary (or initial) interaction of photons with the patient. Typically, this primary energy is then further distributed by secondary particles (electrons, positrons, and photons) until it is absorbed as a dose or it escapes from the bounds of the patient and is no longer of interest. This two step process is the basis for several methods of dose calculation where this distribution of primary energy is convolved with a kernel. The kernel is a three dimensional matrix that describes the distribution of primary energy by the secondary particles. Primary energy released by interaction with a photon does not remain at the interaction site, but is further distributed, and the method of that distribution is known as the kernel. The primary energy distribution is typically referred to as the TERMA, while the kernel is known by many different names (e.g., depending on the author and/or the method). Some names for the kernel include, but are not limited to, differential pencil beams, point spread functions, and/or energy deposition kernels.

Changes in any of the previous components affect the calculation of the TERMA. There are many different TERMA calculation methods which can include a variety of correction factors. It should be noted that the TERMA is, by nature, an approximation of the energy received in a voxel and not an exact measurement. As the TERMA represents an intermediate dose calculation step, it should also be noted that Monte Carlo based radiation dose calculation algorithms have no need to calculate TERMA because they follow the path of each individual photon and only accumulate dose.

A general TERMA calculation is shown in Equation 1.

$$T(r) = (r/r_0)^2 \frac{\bar{\mu}(r)}{\rho(r)} \Psi(r_0) \exp\left(-\int_{r_0}^{r} \bar{\mu}(l) dl\right). \qquad \text{Equation 1}$$

Equation 1 represents an approximate TERMA distribution. In this equation, $\rho(r)$ is the density of the medium at r and $\psi(r_0)$ is the fluence at $r_0$. Of the scalars, r is the current calculation radius (representing the radius of the current point at which the TERMA is being calculated) and $r_0$ is the radius at the phantom surface. Also, $\bar{\mu}$ is the mean linear attenuation coefficient calculated for the medium present at r using the initial, unhardened spectrum through Equation 2.

$$\bar{\mu}(r) = \frac{1}{\psi(r_0)} \sum_i \psi_i \mu(E_i, r). \qquad \text{Equation 2}$$

Discussed below are inhomogeneity concerns, which are important for the collapse cone implementation, and different physical factors affecting how dose is deposited. The human body includes many different types of tissues, all of which have varying densities and properties. These inhomogeneous tissues may affect the calculation of the radiation dose when using the convolution/superposition methods of dose calculation, and are typically the main reason that faster software implementations have not yet been developed. With Monte Carlo methods, dose deposition factors are statistically modeled and inherently included. However, extending the convolution/superposition methods to heterogeneous media is not as simple. To be rigorous, a different kernel would need to be generated for every heterogeneous situation that could be encountered. This is obviously unreasonable as the number of heterogeneous possibilities is significant. Therefore, an acceptable compromise between accuracy and speed/memory use may be employed.

One solution employed is to use range scaling to approximate a new kernel in heterogeneous phantoms. This is typically known as the density scaling method. Persons having ordinary skill in the art will appreciate that results obtained using this method can be off by as much as 50% when compared to the Monte Carlo calculations. However, this difference is much less severe when using realistic photon beams in representative tissue(s).

Figure 2:
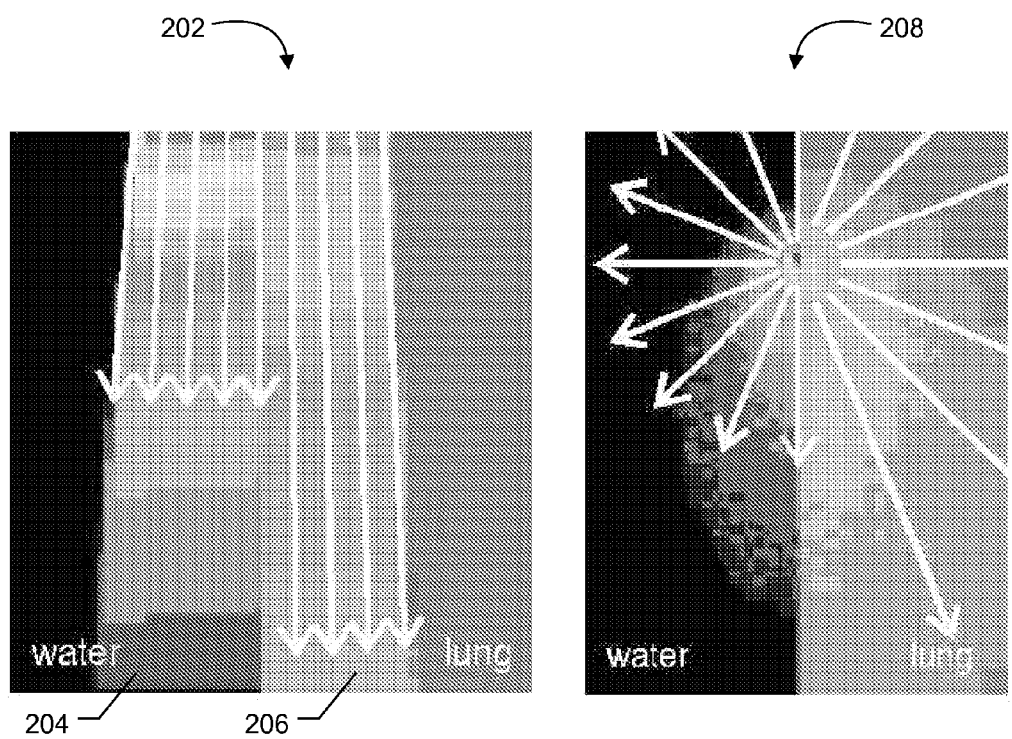
FIG. 2 illustrates example radiation distances for mediums of water and lung tissue.

FIG. 2 illustrates the distance radiation travels in different media. A surface interaction image 202 is shown on the left hand side. The surface interaction image illustrates water on the left 204 and lung tissue on the right 206. The length of the arrows represents the distance radiation travels in the different mediums. A boundary image 208 is shown on the right hand side of FIG. 2, which illustrates an interaction at the boundary between water and lung. Lung tissue is much less dense than water and so radiation travels a greater distance from the interaction site.

Density scaling works by finding the average $\bar{\rho}$ (tissue density) between the interaction and deposition voxels. Kernels computed for a specific $\rho$ (normally water, where $\rho$ 1.0), thus is typically adjusted (scaled) when the $\bar{\rho}$ of the tissue is different from the p of the kernel. Computing this is typically a matter of scaling the distance by a factor of $\rho/\bar{\rho}$. In homogeneous media, simply using a physical distance indicator l is usually sufficient, but with heterogeneous media, a scaling factor is typically used (p*l) to get the radiological path length (rather than the physical path length). Physical path length represents the physical length between an interaction and deposition voxel. Radiological path length represents the radiological distance (relative to that of the available kernel) between the interaction and deposition voxels, and depends on both average density of the material and physical distance.

Dose Calculation

There are several different methods by which the energy of photon beams created as bremsstrahlung, which is the photon radiation emitted by the deceleration of an electron in the Coulomb field of an atom and deposited within a phantom. Once a photon imparts some energy to an electron, the energy from the electron is deposited locally when viewed in relation to the photon. A photon may pass through a patient and only interact at one or two locations, but once the interaction occurs, the energy released to the electron is deposited in a region local to the interaction site (described by the kernel).

As discussed above, there are many different methods used to perform dose calculation. The methods described herein include the FFT (Fast Fourier Transform) method, the Monte Carlo analysis, and convolution/superposition methods. Additionally, details regarding the collapse cone method are described herein, which is a specialized convolution/superposition method.

Fast Fourier Transform (FFT)

It has long been known that convolution in the spatial domain is equivalent to multiplication in the frequency domain. FFTs are a way of converting data given in the spatial domain to the frequency domain. A convolution equation typically would resemble that given in Equation 3.

$$D(i, j, k) = \frac{1}{\rho(i, j, k)} \sum_{i'} \sum_{j'} \sum_{k'} T(i', j', k') H(i-i'), (j-j'), (k-k').$$ Equation 3

In Equation 3, D(i, j, k) is the value of the dose, T(i', j', k') is the TERMA at the interaction site, and H(i-i'), (j-j'), (k-k') is the value of the energy deposition kernel at the deposition site. Also, $\rho$(i, j, k) represents the density of the medium at (i, j, k). This summation is performed over all voxels in the medium where both T(i', j', k') and H(i-i'), (j-j'), (k-k') are not equal to 0. In convolution calculations, it should be noted that the kernel used needs to be invariant, and it can be seen in Equation 3 that the kernel satisfies this constraint. Moreover, the method of dose calculation illustrated above is computationally expensive.

One alternate approach is to take the FFT of both the TERMA matrix and the kernel matrix, which may be accomplished by using any number of FFT conversion algorithms, each of which has benefits of its own. As a result, instead of performing convolution, an element by element multiply of the transformed matrices may be performed, in which the inverse FFT of the resulting matrix is performed to obtain the dose. As it is typically less computationally intense to perform two FFTs, a multiply, and an inverse FFT, this method is quicker that other algorithms.

The FFT algorithm, while quick, does suffer from a number of drawbacks. One such drawback includes a requirement that the kernel used be invariant. Therefore, it becomes more difficult to obtain an accurate dose with heterogeneous media.

Monte Carlo

The Monte Carlo method of radiation dose calculation follows the path of individual particles through the accelerator, beam modifiers, and the patient to determine dose, fluence, and other distributions in patients and phantoms. It uses basic physics interaction probabilities to determine the fate of each particle. As this method is based on probability, there must be a sufficient number of representative particles transported to produce statistically acceptable results.

The Monte Carlo method follows particles recording quantities of interest, such as energy deposition (dose) and fluence. It follows these particles until they are no longer of interest, i.e., they escape the region of interest, the particle is absorbed, or the particle drops below the energy cut-off. To get a statistically valid result, approximately 100 million particles are used during a simulation. Increasing the number of particles simulated increases the computation time linearly, but only improves the accuracy by the square root of the number of particles. Due to repeated use of the same calculation, Monte Carlo methods may also be candidates for hardware implementation.

Figure 3:
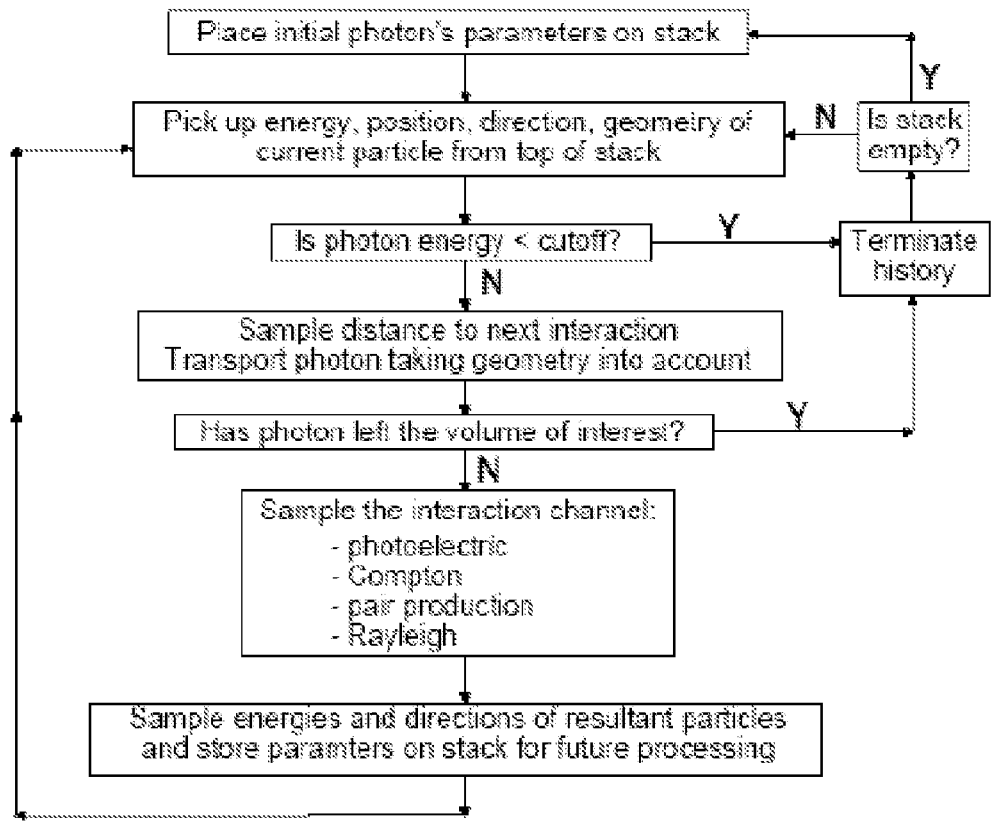
FIG. 3 illustrates an example method of Monte Carlo dose calculation.
Figure 4:
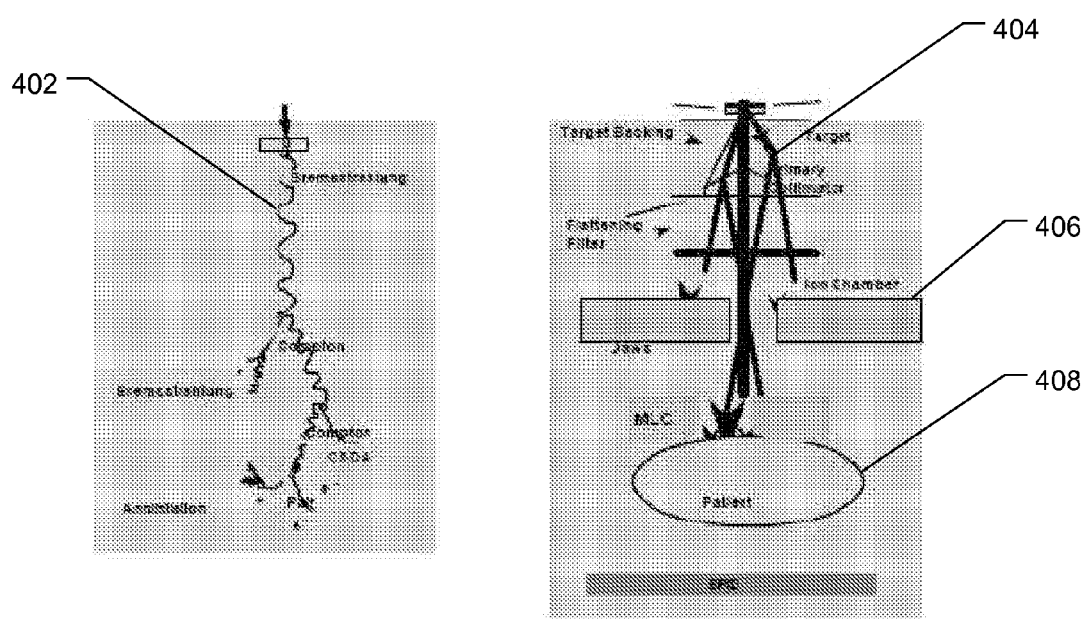
FIG. 4 illustrates example particle interactions within a Monte Carlo method.

FIG. 3 illustrates an example main program flow for Monte Carlo code. FIG. 4 illustrates typical particle interactions within a Monte Carlo program. In particular, an electron path 402 is shown on the left to illustrate a path of individual photons and electrons traced through a phantom. Bremsstrahlung, the Compton effect, pair production, and annihilation can also be observed in FIG. 4, where the solid line is the actual path of the photon/electron. The interaction between an atom and a photon is depicted at the top, with the path of the election(s) being shown below. On the right, an emission path 404 is shown and depicts the emission of radiation from a source, down through jaws 406, and to the patient 408, where the electron path 402 figure (on the left) continues.

Convolution/Superposition

The convolution/superposition method of radiation dose calculation can be thought of as a convolution between the TERMA and the kernel. This convolution can be defined in the manner described by Equation 4

$$D(r)=[1/\rho(r)]\iiiint T_E(s)\rho(s)h(E,s,r)d^3sdE. \quad \text{Equation 4}$$

Typically an algorithm is known as a convolution algorithm if it does not address heterogeneous media, and is known as a superposition algorithm if it does address heterogeneous media. As the general idea is the same between them, they are typically classified together as convolution/superposition algorithms.

When the kernel must be scaled depending on the density of the media, a straight forward convolution approach can no longer be used. Because of this, the convolution method may be changed to allow a varying kernel and the new algorithms use superposition.

Equation 4 shows the calculation of dose in a continuous integral form. In this equation, the (monoenergic) kernel h(E, s,r) of energy E is defined as the fraction of radiant energy released by primary photons at the initial interaction site s which is imparted per unit volume at r. In homogeneous media, the point spread function is spatially invariant and h(E,s,r) is replaced by h(E,s-r). In view of the definition of the TERMA, the radiant energy released from a volume element $d^3s$ of density $\rho(s)$ irradiated by photons of energy E, is $T_E(s)\rho(s)d^3s$ and hence the absorbed dose at r is given by integration over volume and energy as above. The final division by $\rho(r)$ converts the energy imparted per unit volume to energy imparted per unit mass, or dose.

However, it is not typically efficient or feasible to integrate over energy, so the dependence on energy is taken out by using a polyenergetic kernel and calculating TERMA for all energies. The kernel h(E, s, r) presented in Equation 4 is a monoenergetic kernel, while the kernel h(s, r), presented as Equation 5, is polyenergetic.

$$D(r)=f(r)[1/\rho(r)]\iiint T(s)\rho(s)h(s,r)d^3s. \quad \text{Equation 5}$$

In Equation 5, f(r) is a dose hardening correction factor. The above equations provide a general idea of how dose is computed using a superposition approach. While the equations involve integrals, it should be noted that in a discrete implementation, the integrals would be replaced by summations, and the continuously varying functions (TERMA, density, etc.) would be replaced by discrete intervals over which the function would be assumed to be constant. Using discrete intervals, dose would then be accumulated into voxels, rather than continuous points.

Collapsed Cone

The purpose of the collapsed cone convolution algorithm was initially to make it practical to implement the function described in Equation 5. The equation illustrates that the integrals must be evaluated for all combinations of scattering and receiving points, which are time consuming. For each interaction point, there are $N^3$ scattering points or points where dose could be "scattered" to consider, where N is the number of voxels along one side of the matrix. Equation 5 also takes up to N operations to ray-trace between a scattering and receiving point. Therefore, the complexity of this approach would be between $N^6$ and $N^7$ operations.

Figure 5:
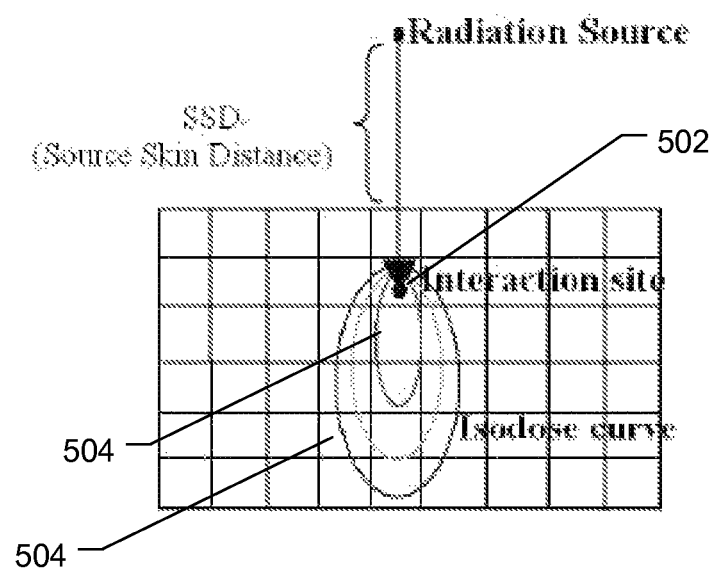
FIG. 5 is an example illustration of a normalized kernel of radiation energy.

Similar to all kernel-based superposition methods, the collapsed-cone algorithm models the radiation energy release as a two-phase process. Phase 1 considers the interaction of photons with the tissue. If an interaction occurs within the phantom, it is assumed that this energy is all deposited at the interaction site. Phase 2 examines energy diffusion. As shown in FIG. 5, the radiation energy is considered to be diffused in a teardrop shape slanted in the direction of the interacting photon 502. A normalized kernel may be used to describe how this energy is distributed in the phantom. The kernel is depicted as isodose curves 504 as shown in FIG. 5.

As described above, there must be a discretation of the components mentioned in Equation 5. In dose planning, the target spatial resolution of this discretation is typically between 0.1 to 1 cm. In this range, the TERMA is slowly varying and no sizable errors are introduced with its discretation. The energy deposition kernels have very steep gradients within the same range. Therefore, the discretation of the kernel typically results in very small gradients close to the interaction site and larger gradients as distance from the interaction site increases.

Figure 6:
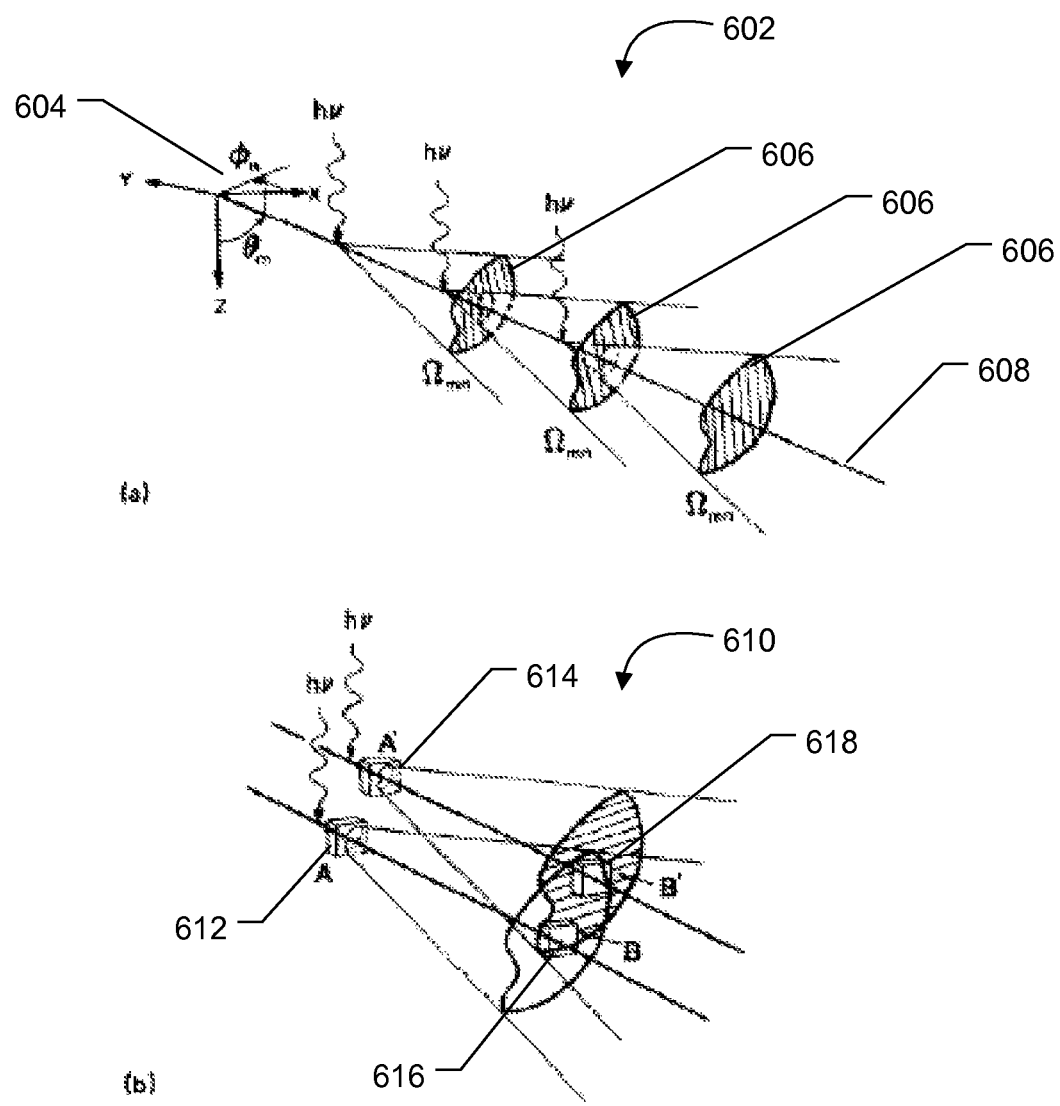
FIG. 6 is an example illustration of a collapsed cone approximation of radiation energy.

Collapsed cone approximation is shown in FIG. 6. The "Collapsed Cone" approximation is made in the manner described below. All energy released into coaxial cones, of solid angle $\Omega_{mn}$ from volume elements on the axis are rectilinearly transported, attenuated and deposited in elements on that axis. This allows for accurate computation of the dose deposited to all voxels while performing fewer computations: The dose may be calculated using $M*N^3$ calculations, where M is the number of cones (typically between 48 and 384) and N is the number of Cartesian voxels along one side (i.e., there are $N^3$ voxels). The FFT Method previously described requires $(2N)^3 * \log_2 2N$ and has the problem of requiring an invariant kernel. In the illustrated example of FIG. 6, a collapsed cone approximation 602 illustrates all energy released from primary photos at elements on a cone axis 604 of direction $(\theta_m, \Phi_n)$ and flowing in coaxial cones 606 of solid angle $\Omega_{mn}$, is rectilinearly transported and deposited on an axis 608. In the illustrated example, to transport all energy released, several cone axes are used such that $\Sigma_{m,n}\Omega_{mn}=4\pi$, and parallel axes of each direction cover the irradiated volume. While the example collapsed cone approximation 602 of FIG. 6 illustrates one axis, an infinite number of axes, where $\Omega_{mn} \rightarrow 0$, yields a continuous case of rectilinear motion. An interaction point 610 is shown in FIG. 6, in which a cone covers only a fraction of a Cartesian voxel, as shown by voxel "A" 612 and voxel "A'" 614. Additionally, FIG. 6 illustrates off-axis voxel "B" 616 and off-axis voxel "B'" 618. In the collapsed cone approximation, the energy that should have been deposited in voxel "B'" 618 from interactions at the vertex of the lower cone is deposited in voxel "B" 616, and vice-versa. As a result, the relative accuracy of the calculated energy deposition decreases with the distance from the scattering point. The error is small because the magnitude of polyenergetic point spread functions decreases rapidly with the distance from the interaction point.

Kernel Calculation

Several equations are described below to accurately compute dose using the collapsed cone approximation, which relate to hardware implementation. Described below are two example methods used to calculate the kernel for the convolution/superposition class of dose calculation algorithms. A first example method includes using Monte Carlo analysis. A second method employs exponential functions for reproducing a kernel. It should be noted that even with the exponential kernel, Monte Carlo may still be used to generate the original data points, and then regression may be applied to find the exponential values used for the kernel.

EGS (Electron Gamma Shower) Monte Carlo code may be used to generate energy deposition kernels. The EGS code is a general purpose photon-charged-particle transport simulation system, which may be used for medical physics. It was originally developed at SLAC (Stanford Linear Accelerator Center) to describe the transport through matter of photons and charged particles from very high-energy linear accelerators and cosmic rays.

The EGS code may generate monoenergetic kernels of energies varying from 0.1 to 50 MeV. These kernels can then be used in convolution calculations to produce dose distributions. Additionally, they may be repeated for each spectral component of the photon beams. Photon beams are not monoenergic, but rather contain multiple different energies. Polyenergetic kernels may also be composed for a spectrum by weighting multiple monoenergetic kernels by their respective contribution to the spectrum. These kernels can then be scaled to other mediums.

The zone dominated by scattered photons of monoenergetic kernels is described accurately by an exponential, B exp(−b|r|)/|r|$^2$, where B and b depend on the energy and the angle of r versus the direction of the impinging primary photon, and r is the radius from the interaction point. Polyenergic kernels may be described by a similar function shown in Equation 6.

$$h_w(r,\theta) = (A_\theta e^{-a\theta r} + B_\theta e^{-b\theta r})/r^2. \qquad \text{Equation 6}$$

Figure 7:
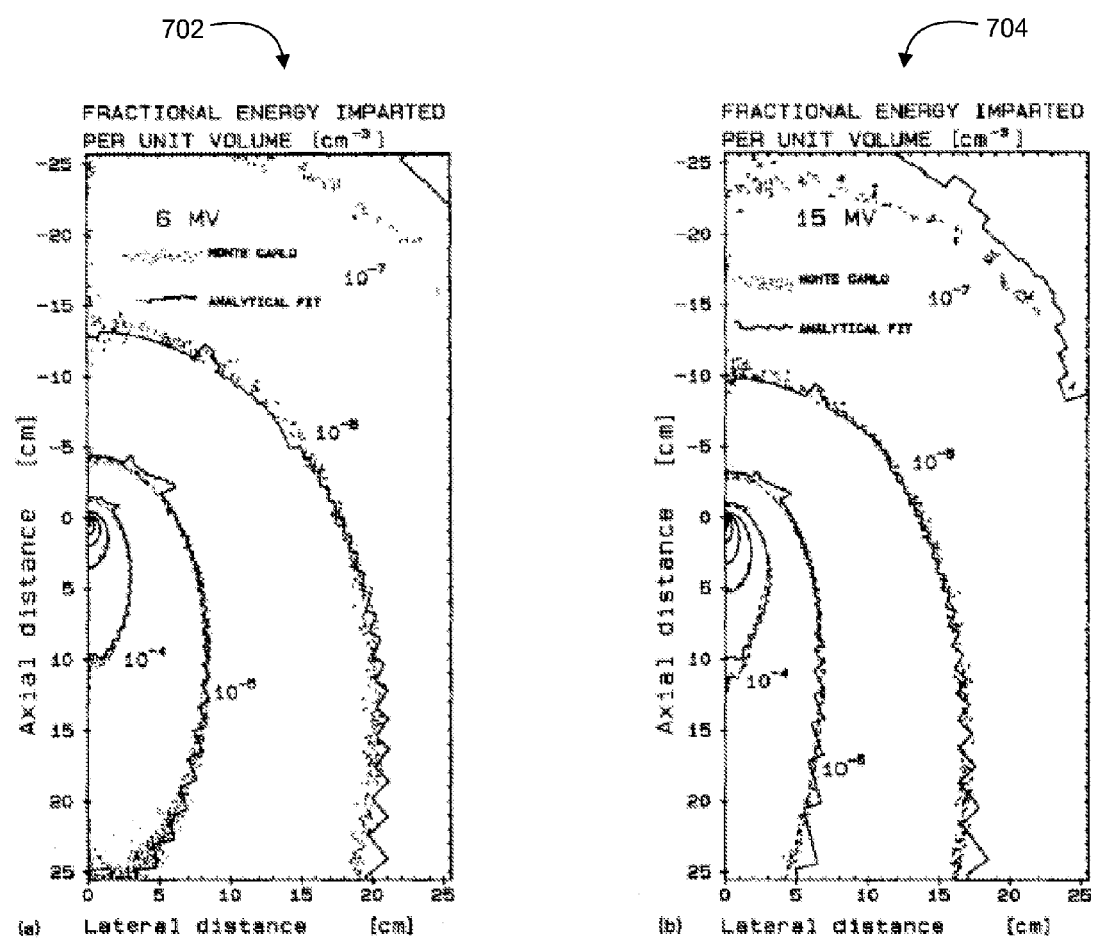
FIG. 7 is an example plot of energy deposition kernels of photons in water.

In this equation, $A_\theta$, $a_\theta$, $B_\theta$, and $b_\theta$ are functions of the scattering angle $\theta$ and the accelerating potential (e.g., 10 MV). Scattering angle refers to the angle that the receiving point is (in spherical coordinates) at in relation to the interaction point, while the accelerating potential is a function of the particular linear accelerator used. FIG. 7 illustrates that there is good agreement between the exponentially calculated kernel and one generated using Monte Carlo analysis. A 6 MV energy plot 702 and a 15 MV energy plot 704 are shown in FIG. 7. These figures illustrate deposition kernels for photons in water, in which the thin, hatched lines were calculated with Monte Carlo, and the thick, solid lines are corresponding analytical fit curves.

Typically, kernels are stored in memory and then loaded each time they are required. However, FPGAs typically contain very limited memory bandwidth, thereby illustrating a benefit to calculate a kernel rather than loading one. FIG. 7 also illustrates that using the exponentially calculated kernel does not adversely affect calculation accuracy. To use the kernel in heterogeneous mediums, a density scaling method is applied, as shown in Equation 7.

$$h(r, \theta, \phi) = \eta(r, \theta, \phi)\left(A_\theta e^{-a\theta \int_0^r \eta(t,\theta,\phi)dt} + B_\theta e^{-b\theta \int_0^r \eta(t,\theta,\phi)dt}\right)/r^2. \qquad \text{Equation 7}$$

Here, $\eta(r, \theta, \Phi)$ is a spatially varying function representing the ratio of electrons per unit volume (relative to water) and the r value previously in the exponent has been changed from the physical path length to a quantity representing the radiological path length.

The collapsed cone algorithm differs from other existing work in dose calculation in at least two aspects. First, analytical kernels are used, which may be approximated analytically (in homogeneous media) as shown in Equation 8.

$$h(r, m) = \eta \frac{A_m e^{-a_m \eta \Delta r} + B_m e^{-b_m \eta \Delta r}}{r^2}. \qquad \text{Equation 8}$$

In Equation 8, q is the relative electrons density (relative to water), m is the zenith angle, $A_m$, $a_m$, $B_m$, and $b_n$ are fitting coefficients depending on m. The dose equation for monoenergetic irradiation of a homogeneous phantom is shown in Equation 9.

$$D(r) = \iiint_V T(s)h(r-s)d^3s. \qquad \text{Equation 9}$$

In Equation 9, T(s) is the TERMA from the primary photon energy fluence in the volume element d$^3$s. The second key feature of the collapsed cone algorithm is its assumption that the energy released into a cone can be approximated by the energy deposited on the cone's axis. Based on this assumption, the collapsed cone algorithm may reduce the computational complexity of the dose calculation to O(N$^3$M), where N is the number of voxels along one side of the tissue matrix, and M is the number of cones used.

Figure 8:
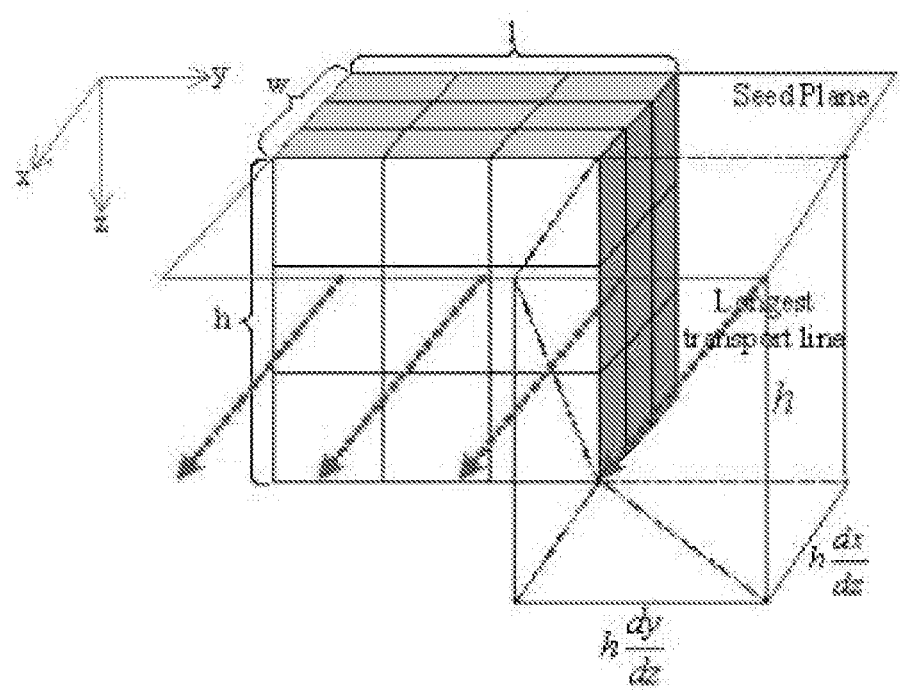
FIG. 8 illustrates an example seed plane with transport lines for an area of interest.

To further accelerate the dose calculation by the collapsed cone algorithm, the cone axes from different voxels may be overlapped. Instead of building individually the local polar system for each voxel with non-zero TERMA, a lattice structure, referred to as transport lines, may be used to represent the cone axes for each cone direction in the computation of energy deposited into the area of interests (AOI). For a given direction cosine $\{d_x, d_y, d_z\}$, to ensure that the transport lines are able to cover the whole AOI, the concept of a seed plane from which the transport lines originate is used. An example seed plane and some of the transport lines originated from the plane is shown in FIG. 8 for an AOI with the dimensions w×l×h.

The placement and area of the seed planes may have an impact on hardware resource usage and performance. In particular, at least one goal includes minimizing the area of each seed plane such that the transport lines originating from the plane cover all of the voxels in the AOI as few times as possible. A first step may include selecting the tissue surface for which an "inward" normal maximizes a scalar product with a direction cosine vector $\{dx, dy, dz\}$. For example, in FIG. 8, assume that the $|d_z|$ is the largest. As such, the top surface of the AOI is selected because d is positive. A second step may include generating a seed plane by expanding the tissue surface identified above along the other two directions. If the direction cosine is negative, the tissue surface is expanded towards the positively increasing direction, and vice versa. For example, in FIG. 8, the top tissue surface is expanded along the positive s and y directions by $$h\left|\frac{d_x}{d_z}\right|$$

and $$h\left|\frac{d_y}{d_z}\right|,$$

respectively, because $d_x$ and $d_y$ are both negative.

Based on the ideas of the seed plane and lattice, the radiation energy deposited into the voxels along the transport lines can be computed iteratively. The dose is considered to include at least two parts: the primary dose and the scattering dose. The former mainly comes from charged particles released by the first interaction of a primary photon, whereas the latter is the result from charged particles set in motion by secondary photons. The final dose for the voxel at r(i) is the sum of the primary dose and the scattering dose, as shown below in Equation 10.

$$D_{mn}(r_i) = D_{mn}^p(r_i) + D_{mn}^s(r_i). \qquad \text{Equation 10}$$

The primary dose $D^p_{mn}(r_i)$ for a voxel $V_d$ at $r_i$ is shown in Equation 11.

$$D^p_{mn}(r_i) = D^s_{mn}(r_{i-1})a_m e^{-a_m\eta\Delta r} + T\Omega_{mn}\frac{A_m}{a_m}(1 - e^{-a_m\eta\Delta r}).\quad\text{Equation 11}$$

The first term is the dose contribution to $V_d$ from the voxels previous to $V_d$ along the transport line, which attenuates exponentially along the line. The second term is the dose contribution from voxel $V_d$ to itself, where T is the TERMA and $\Omega_{mn}$ is the solid angle of the cone. Similarly, the scattering dose for the voxel can be calculated as shown in Equation 12.

$$D^s_{mn}(r_i) = D^s_{mn}(r_{i-1})b_m e^{-b_m\eta\Delta r} + T\Omega_{mn}\frac{B_m}{b_m}(1 - e^{-b_m\eta\Delta r}).\quad\text{Equation 12}$$

Field Programmable Gate Arrays

One or more FPGAs may be used for implementation of radiation dose calculation in hardware. An FPGA is a FPD (Field Programmable Device) featuring a general structure that allows very high logic capacity. Unlike CPLDs (Complex Programmable Logic Devices), which offer a wide number of functional inputs, FPGAs typically offer narrower logic resources. In addition, FPGAs typically possess many more flip-flops than do CPLDs.

Figure 9:
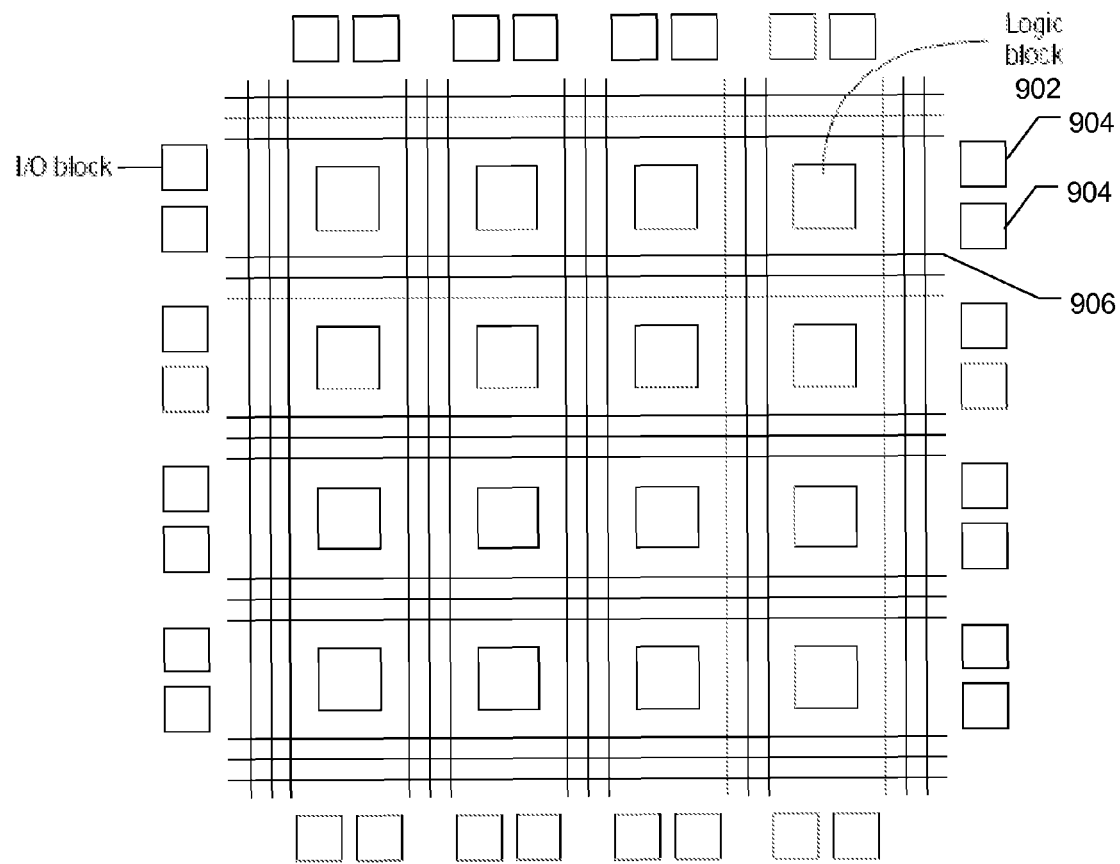
FIG. 9 illustrates an example Field Programmable Gate Array (FPGA) structure.
Figure 10:
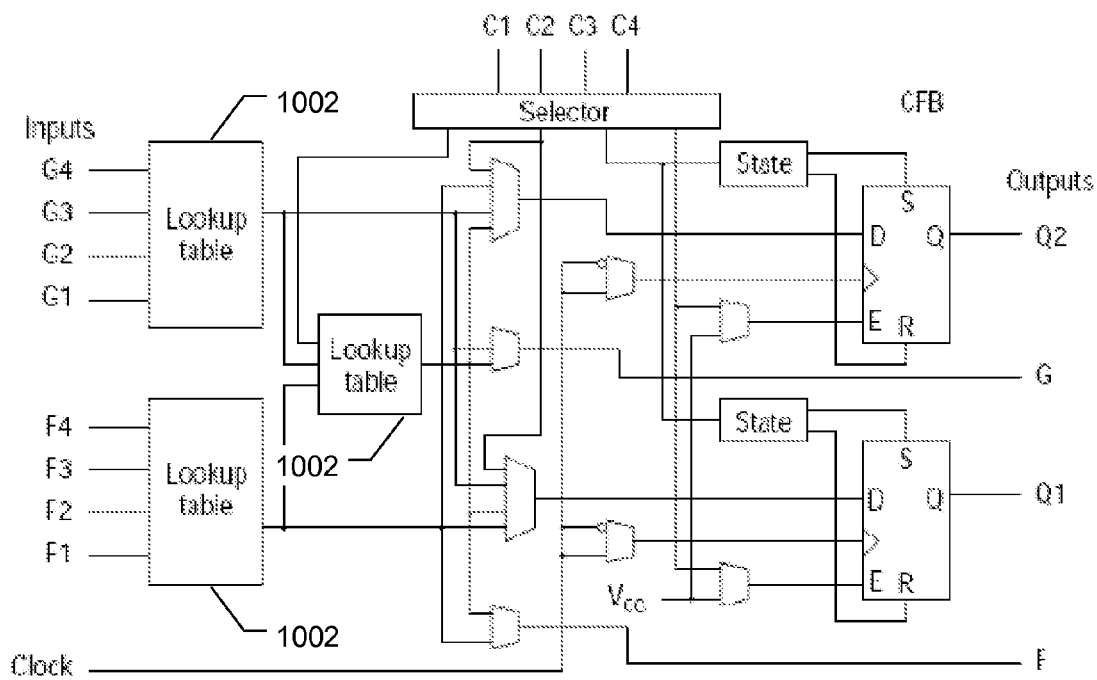
FIG. 10 illustrates an example configurable logic block implemented with lookup tables.

FPGAs usually possess logic blocks surrounded by interconnect resources. These logic blocks may be configured to perform different functions by the end user through programming A typical FPGA structure is shown in FIG. 9. In the illustrated example of FIG. 9, logic blocks 902 are arranged so that they are bordered by interconnect resources 904. Pin inputs and outputs 906 are arranged along the outside of the chip. Additionally, FIG. 10 illustrates an example of a XILINIX® CLB (Configurable Logic Block). In the illustrated example of FIG. 10, the CLE is implemented with lookup tables 1002. In general a k-input logic function may be realized with a $2^k \times 1$ bit lookup table by programming a truth table into the memory. The configuration of the XILINIX® CLBs allow for a single nine-input function, two separate four-input functions, or other possibilities. In this way, the CLBs are very flexible and adaptable to a wide variety of applications.

Figure 11:
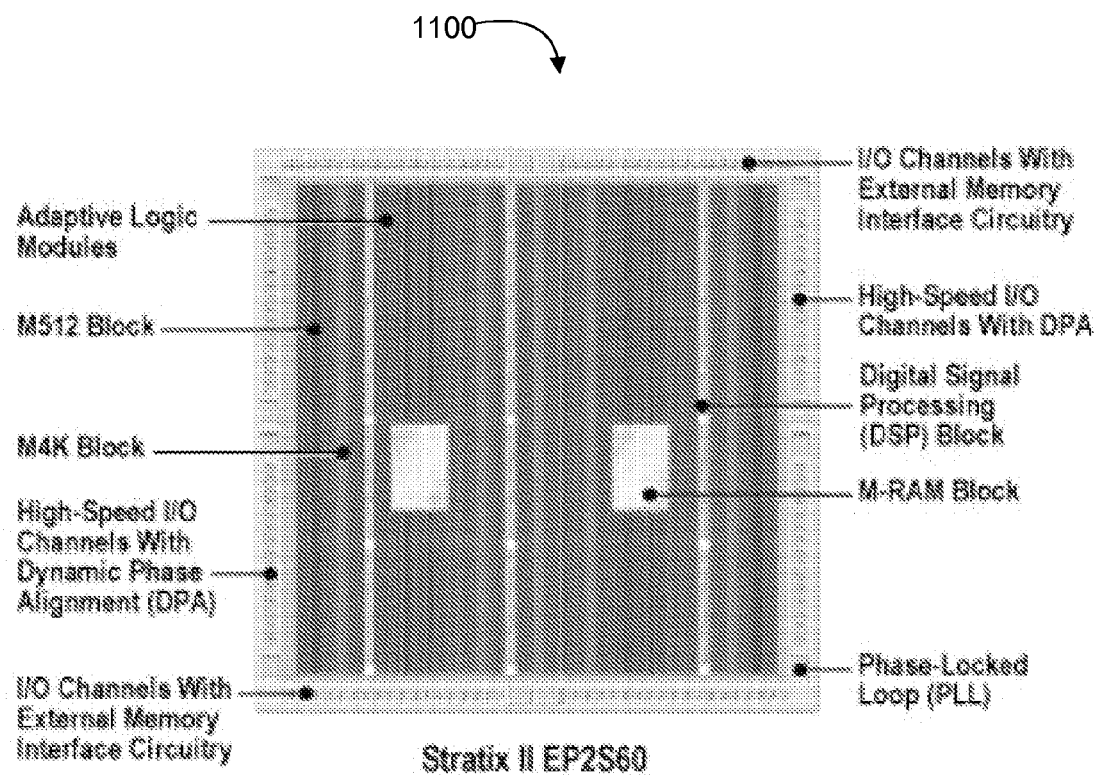
FIG. 11 illustrates an example commercial FPGA with embedded arithmetic units and embedded memory.

In addition to simple logic blocks, many modern FPGAs also incorporate embedded memory and embedded arithmetic units. For example, Altera FPGAs contain embedded (Tri-Matrix) memory in varying amounts on different chips along with embedded arithmetic units (Digital Signal Processing Blocks). The structure of an example STRATIX II® device 1100 manufactured by Altera showing these embedded memories and arithmetic blocks can be seen in FIG. 11.

Until recent years, FPGAs were not considered viable candidates for floating point arithmetic because such floating point operations typically require excessive time and area (silicon) to implement. However, through recent advances in technology (e.g., embedded memory, increased logic density, or the addition of embedded arithmetic blocks), significant increases now exist in the ability of the FPGA to compete with the microprocessor in terms of floating point performance.

Previously, FPGAs were considered alternative candidates to the CPU only if a fixed point algorithm or an algorithm using only a small dynamic range were used. However, starting in 1995, people began to believe that FPGAs could compete in the floating point domain. Various developments resulted including, but not limited to, floating point adders, subtracters, multipliers, and dividers using 16 and/or 18 bit floating point formats. The introduction of high level languages such as VHDL, along with advancements in technology helped make feasible the implementation of these floating point operations on FPGAs.

Persons having ordinary skill in the art will appreciate that floating point calculation is typically more efficient than fixed point calculations when the dynamic range of the numbers used are large. Libraries typically offer the user the ability to customize their design to a particular floating point format.

Many such libraries offer compliance with an IEEE-754 standard for floating point arithmetic, while at the same time allowing the user the flexibility to break that compliance when unnecessary. For example, a large number of logic elements are typically needed to implement certain features of the IEEE-754 standard. These features include gradual underflow (especially in a multiplier), overflow protection, and the use of different rounding modes. If these functions are not needed, as gained by knowledge of the input operations or processing flow, then they can be excluded from the implementation of floating point units, thus decreasing both latency and area.

In the future FPGAs may be more efficient, in terms of peak MFLOPS (Millions of Floating Point Operations Per Second), than CPUs in performing all types of floating point operations and that currently they are capable of performing more MFLOPS than CPUs at most floating point operations. Currently, FPGAs usually beat out CPUs in performing the floating point operations of addition/subtraction, division, and multiplication. However, some FPGAs lag behind in the DSP operation of multiply-accumulate. According to Moore's law, there is a 2× increase in the density of logic every two years and a 2× increase in the clock rate every two years, leading one to expect a 1× increase in performance for FPGAs. This is higher than the 4× increase in CPU performance every three years. Also, things such as embedded 18×18 multipliers on some chips have enabled substantial gains in floating point multiplication. Floating point multiplication in FPGAs in terms of peak MFLOPS has been growing at the rate of 5× per year over the past six years.

FPGAs are able to implement some algorithms substantially faster than CPUs. They allow the user to perform several operations in parallel and hence speed up the computation. However, this is not the only reason that FPGAs are faster than CPUs. While it is true that FPGAs obtain performance increases due to extraction of parallelism from algorithms, it should also be noted that FPGAs typically run at much slower clock speeds than CPUs. A typical speed for an FPGA is from 30-100 MHz, and embedded processors run between approximately 100-600 MHz. Even after accounting for the frequency differences, the speedup of FPGAs over CPUs was still one to two orders of magnitude.

FPGAs offer advantages over CPUs in the areas of iteration parallelism, the number of necessary operations, efficiency, and number of memory operations. Iteration parallelism refers to the fact that an FPGA could execute many iterations of a loop at once provided there are no loop carry dependencies. FPGAs also decrease the number of necessary operations. Operations such as a shift or a multiply by a power or two are accomplished without the use of a clock cycle on an FPGA. The efficiency advantage is gained since there are no support instructions that need to be executed.

The reduction in memory operations may come from the large number of embedded registers and on-chip memory that allow the FPGA to avoid continuous reads from slower off-chip memory that may need to be performed in a CPU.

FPGAs allow the user to configure on-chip storage at will and customize it for each loop. In particular, this storage can be used to efficiently reduce the number of memory accessing by reusing data, which results in an 8-14× reduction in memory use.

During development and testing of the methods and apparatus described herein, three different image processing applications were evaluated: Prewitt edge detection, wavelet transform, and maximum filter. For the three applications, the use of an FPGA resulted in speedups of 312 times (Prewitt), 210 times (wavelet transform), and 226 times (maximum filter) over a PENTIUM® processor performing the applications. Accordingly, even though FPGAs have a much slower clock speed than a CPU, they are much more efficient at performing arithmetic operations. As such, persons having ordinary skill in the art will appreciate that the methods and apparatus described herein may have applications beyond dose calculation algorithms. While creating radiation dose calculation is described herein as one objective, the methods and apparatus described herein may be applied, without limitation, to many other objectives. For example, other such processing objectives may include image processing.

Dose Calculation Hardware

Direct convolution may be applicable in situations involving homogeneous media. While these conditions do not necessarily occur often in practice, it is useful to have a fast convolution model that is capable of handling these situations when they do occur. For situations involving inhomogeneous media, the collapse cone algorithm may be used, as described in further detail below.

In the convolution algorithm(s) described herein, the parallelism inherent in convolution may be exploited. These solutions can also take advantage of future improvements in hardware, employ variations of the algorithms described herein, and may be easily ported to alternate FPGAs, as needed. Here, large decreases in convolution time have been achieved when compared with a typical single processor computer system. As described in further detail below, dose calculations based on FPGA hardware implementations allow calculation speed improvements in view of direct convolution/superposition methods, collapsed cone methods from an interaction point of view, and/or collapsed cone methods from a deposition point of view.

Direct Convolution

A three-dimensional (3-D) convolution system is described herein and configured as an SoPC that may include various elements to make up the entire system. Additionally, a two level parallel structure is described in further detail below. Persons having ordinary skill in the art will appreciate that either of these systems may be employed to calculate radiation dose, depending on, for example, particular hardware availability and/or capability.

Figure 12:
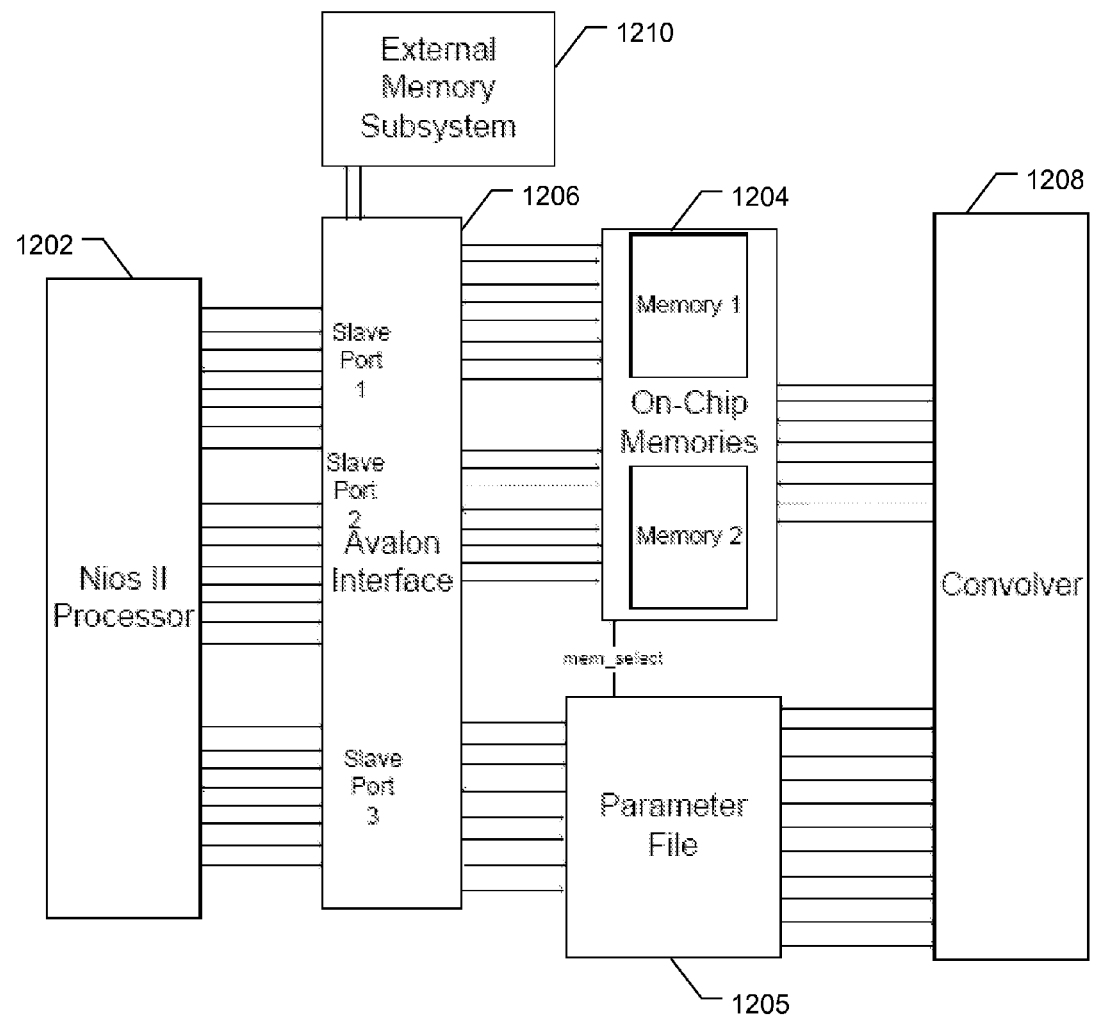
FIG. 12 is a block diagram of an example three-dimensional convolution system.

As shown in FIG. 12, some of the elements of the example 3-D convolution system include an embedded soft-core processor 1202, embedded memories 1204, a register file 1205, an AVALON® interface 1206 (which is a proprietary high-bandwidth interconnect structure from Altera), and a convolver 1208. FIG. 12 also illustrates a general overview of the system and shows the connections between the different components.

In the illustrated example of FIG. 12, the embedded soft-core processor 1202 is implemented as a NIOS II® soft-core processor, which serves as a bridge between the convolver 1208 and external memory 1210, as well as a bridge between the convolver 1208 and any external off-chip communication. Accesses to off-chip memory (e.g., SDRAM, SRAM, etc.) and the use of input or output pins (such as use of the Ethernet interface on the development board) may be controlled by the NIOS II® processor. The NIOS II® processor also controls which embedded memory the convolver can access along with when the convolver begins its computation.

The convolver 1208 is a block which computes a single two-dimensional (2-D) convolution. Accordingly, the convolver 1208 utilizes data in one of the embedded memories 1204 and information contained within the register file to complete this convolution. Communication with the NIOS II® processor 1202 may be handled by, for example, the AVALON® interface 1206, as described in further detail below. The register file 1205 simply contains a bank of registers that are used to communicate information either to or from the convolver 1208.

The embedded memories 1204 in the convolution system may store a single plane of the convolution matrix, the kernel matrix, and the result matrix. In view of the possibility that the size for each 3-D matrix can reach 100×100×100, the embedded memories 1204 need to be able to store three matrices of size 100×100 each. In the illustrated example of FIG. 12, the current maximum number of bits that can be used to represent a result in any of the memories 1204 is 32. As shown below, Equation 13 can be used to calculate the size of one of the two on-chip memories 1204 illustrated in the example SoPC of FIG. 12.

$$\begin{aligned}\text{Memory\_Size} &= \text{Number\_Of\_Matrices} * \\ &\quad \text{Size\_Of\_Matrices} * \\ &\quad \text{Number\_Of\_Bits} \\ &= 3 * (100 \times 100) * 32 \\ &= 960,000 \text{ bits.}\end{aligned} \quad \text{Equation 13}$$

As can be seen in FIG. 12, there are two example embedded memories 1204 present in the example convolver system that are used in a manner similar to that of a double buffer. At any given time, only one of the memories 1204 can be accessed by the NIOS II® processor 1202, while the other memory is used by the convolver 1208. The task of the system is to record the results of the previous convolution and fill the memory 1204 with the necessary data to compute the next convolution. The convolver 1208 uses registers 1205 to identify starting locations of the convolution, kernel, and result matrices. These registers 1205 may be used to determine where to load and store data in the embedded memory to perform a 2-D convolution.

The example embedded memories 1204 used in the convolution may be constructed using the Altera altsyncram megafunction, which implements a parameterized true dual-port RAM using embedded memory blocks on the example FPGA. Parameters and their values that differ from the defaults are listed in Table 1. On-chip memory may be used due to its lower latency compared to off-chip memory.

TABLE 1

Description of the Parameters Used for the ALTSYNCRAM Megafunction

| Parameter | Description | Value |
| --- | --- | --- |
| NUMWORDS_A | Number of words stored in memory | 30,000 |
| NUMWORDS_B | Number of words stored in memory | 30,000 |
| WIDTH_A | Specifies the width of the data_a[ ] input port | 32 |
| WIDTH_B | Specifies the width of the data_b[ ] input port | 32 |
| WIDTHAD_A | Specifies the width of the address_a[ ] input port | 15 |
| WIDTHAD_B | Specifies the width of the address_b[ ] input port | 15 |

Based on the size of the example embedded memories, 3 clock cycles are consumed to access a particular location. Such accesses are pipelined, so the latency of the access is 3 cycles/word, while the throughput is 1 cycle/word given the example current cycle speed of 20 ns (50 MHz). As the access pattern of the memory is known in advance and due to the nature of the convolution, the latency of the memory may be completely shadowed.

In the illustrated example, the embedded memories 1204 are controlled through the register file 1205 and the example NIOS II® processor 1202. The processor 1202 sends a command to the register file 1205 instructing it as to which embedded memory 1204 the processor 1202 will control and which embedded memory 1204 the convolver 1208 will control.

The operation of convolution typically has regular memory access patterns. It can also be memory bandwidth intensive if not utilized correctly. As discussed in further detail below, it is first determined if placement of an entire 2-D convolver will work with the example FPGA. Second, the situation is examined by which only a single 1-D convolver may be accommodated by the FPGA.

Initially, it is assumed that an entire 2-D convolver may fit on the FPGA chip. The ability to do this is typically dependent on the logic elements available on-chip rather than the memory. Additionally, it is assumed that the logic elements are available and simply look at the memory required to overshadow memory access latency with computation. If the example convolution matrix is of size k×i×j and the example kernel is of size t×r×s, then the maximum size for each of these matrices are 100×100×150. Given those sizes, and the sizes of some on-chip memories in FPGAs, it may not be possible to place the entire matrix on-chip. For example, some FPGA chips currently possess around a maximum of 9 Mb of on-chip memory. Assuming that each reference is 32 bits, a single matrix would consume approximately 45.8 Mb, which is a factor of 5 larger than the amount of memory currently available on some of the largest FPGA chips to date.

The on-chip memory needed to perform a 2-D convolution may be much less than that required for the entire matrix. Adequate memory may be needed to create shift registers, and to store one plane of the kernel matrix, the convolution matrix, and the result matrix. The number of bits for each type of matrix, and the amount of memory needed for each of the above is presented in Table 2.

TABLE 2

Representation of Bits Required for Different Convolution Matrices

| Matrix Name | Number of Bits |
| --- | --- |
| kernel | kernel_bits |
| matrix | matrix_bits |
| result | result_bits |

TABLE 3

Amount of On-Chip Memory Required to Perform One Plane of Convolution

| Memory Use | Amount Required |
| --- | --- |
| 1 plane of kernel | s * r * kernel_bits |
| 1 plane of matrix | i * j * matrix_bits |
| 1 plane of result | i * j * res_bits |
| shift registers | (s − 1)*(i − r + 2 * [r/2])*res_bits |

Memory reuse occurs because it is typically not possible to fit the entire 3-D convolution onto the FPGA chip. However, any such limitations of the state of the art of FPGAs are not to be construed as a limitation to the methods and apparatus described herein. Each matrix plane is reused O(k) times throughout this example convolution. However, the amount of memory accessed between each reuse is O(k*i*j*matrix_bits) bits. For example, if matrix_bits is 32, this amount of memory may be too great to be placed on-chip for some FPGAs.

Although some FPGAs may not accommodate adequate on-chip memory for the next plane, it is possible to utilize other memory to prepare the next plane for the convolution function. In the illustrated example, every convolution result takes O(1) clock cycles to compute, and two cycles are used to compute each convolution result. While this might change to one or three or more clock cycles were the implementation changed, it would still require a constant number of cycles to compute the convolution and return a result. Therefore, awareness is maintained to track the number of convolution results that must be obtained before a new plane is needed.

A new plane of the result and matrix matrices is needed after every i*j convolution results. That means that after O(i*j) clock cycles there is a transfer of approximately 2*I*j* (matrix_bits+results_bits) memory bits. In view of the speed of memory devices placed on some FPGA boards, this may be difficult to achieve.

Continuing with the example constraint that an FPGA cannot fit an entire 2-D convolution on-chip, the 1-D convolver approach is described further. With this method, there are no shift registers needed. The memory required for data that needs to be placed in memory is shown below in Table 4. As shown below, only one row of the kernel, one row of the matrix, and one row of the result is needed.

TABLE 4

Amount of On-Chip Memory Required to Perform One Row of Convolution

| Memory Use | Amount Required |
| --- | --- |
| 1 row of kernel | r * kernel_bits |
| 1 row of matrix | I * matrix_bits |
| 1 row of result | i * result_bits |
| shift registers | none required |

In the illustrated example, convolution can be performed only on one row at a time, thus each row of the matrix and kernel is now reused more times. Each matrix and result row is used O(j*k) times. Each kernel row is used O(k) times. In the illustrated example, the number of convolution elements that must be computed between each reuse of matrix and result is now only O(i*j). Therefore, to experience the benefits of data reuse, at least one plane of result and matrix must be stored on-chip. If this amount of memory cannot be fit on an example chip, then the data would have to be reloaded every time. Assuming that an entire plane of matrix and result can be stored on-chip, then each row may be reused O(j) times.

Figure 13:
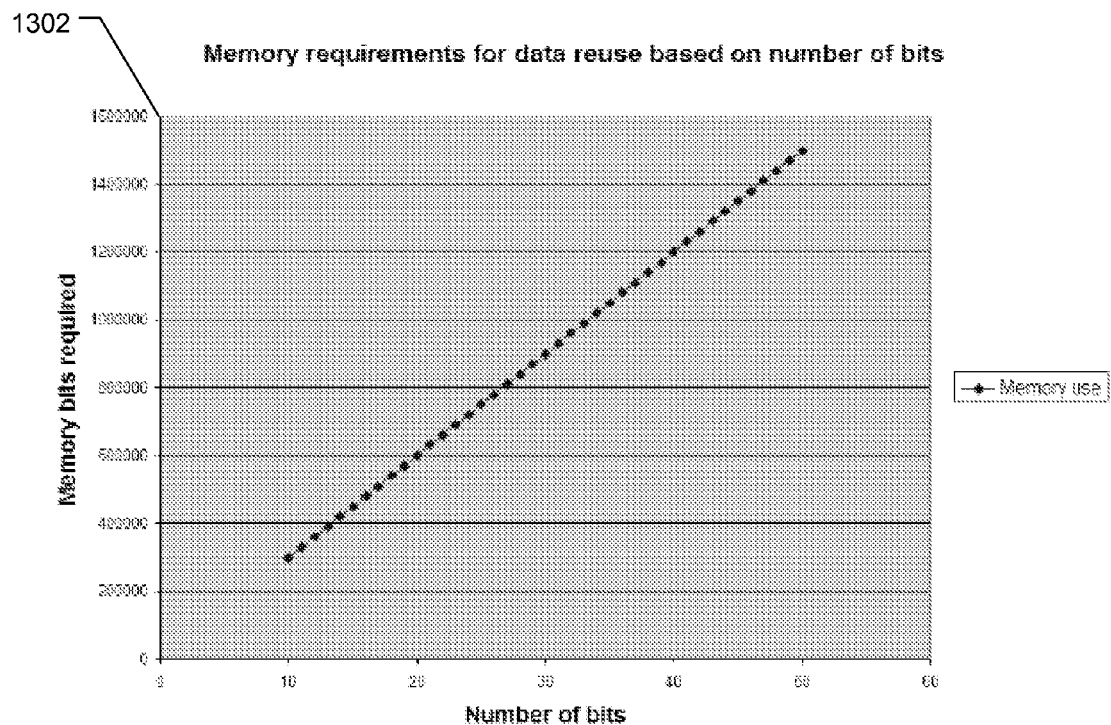
FIG. 13 is an example plot of memory usage for data reuse.

FIG. 13 shows the total amount of memory needed on-chip to experience data reuse, depending on the bit size of different fields. In the illustrated example, it is assumed that the bit size of each matrix is initially 32 bits (which is typical for a floating point number in C) and it is varied both up and down from there. As shown in FIG. 13, the y-axis 1302 represents the total number of bits required for one plane of matrix, result and kernel.

A new row of the result and matrix matrices is needed after every i convolution results. As such, after O(i) clock cycles, there is a transfer of approximately 2*i*(matrix_bits+results_bits) memory bits. This is essentially a linear decrease from the amount of time required in the 2-D convolver case described above. This means that if the memory bandwidth is capable of handling the above case, then it should also be able to handle this case.

The register file contains the registers needed to control the convolver. In the illustrated example, there are a total of 9 different registers that ensure correct functioning of the convolver. The names and purpose of each register are shown below in Table 5, and referring once again to FIG. 12, it can be seen how the register file fits into the overall convolver system.

TABLE 5

Description of the Registers Used in the Convolution System

| Register Name | Description |
| --- | --- |
| conv_start | Signals the convolver to start |
| cony_finished | Indicates whether the convolver is finished |
| matrix_start | Starting address of the convolution matrix |
| kernel_start | Starting address of the kernel matrix |
| result_start | Starting address of the results matrix |
| conv_height | Number of rows for the next convolution |
| conv_width | Number of columns for the next convolution |
| kernel_height | Number of kernel rows for the next convolution |
| kernel_width | Number of kernel columns for the next convolution |
| mem_select | Controls the connection of the embedded memories |

Table 6, shown below, defines parameters used in describing the width and acceptable value of the registers. In Table 7, more information about the different registers is shown, including width and acceptable input values. The column labeled 'Accepted Values' lists all accepted values for the register, or presents an integer range of acceptable values.

TABLE 6

Parameters Describing the Function of the Register File

| Parameter Name | Value |
| --- | --- |
| Width_Address | 15 |
| Max_Conv_Height | 25 |
| Max_Conv_Width | 25 |

TABLE 6-continued

Parameters Describing the Function of the Register File

| Parameter Name | Value |
| --- | --- |
| Max_Kernel_Height | 25 |
| Max_Kernel_Width | 25 |

TABLE 7

Values of Different Parameters for Each Register

| Register Name | Width (bits) | Accepted Values |
| --- | --- | --- |
| conv_start | 1 | 0,1 |
| conv_finished | 1 | 0,1 |
| matrix_start | Width_Address | {0..30,000} |
| kernel_start | Width_Address | {matrix_start..30,000} |
| result_start | Width_Address | {kernel_start..30,000} |
| conv_height | log Max_Conv_Height | {0..Max_Conv_Height} |
| conv_width | log Max_Conv_Width | {0..Max_Conv_Width} |
| kernel_height | log Max_Kernel_Height | {0..Max_Kernel_Height} |
| kernel_width | log Max_Kernel_Width | {0..Max_Kernel_Width} |
| mem_select | 2 | 00,01 |

The NIOS II® processor is able to read and write to all of the registers in the design, with the exception of conv_finished, from which it may only read. The convolver may read all registers, but only affect the value of the convolution_finished register. In this manner, the convolver is able to signal to the processor that it is finished, and the processor is able to communicate all necessary information to the convolver.

Figure 14:
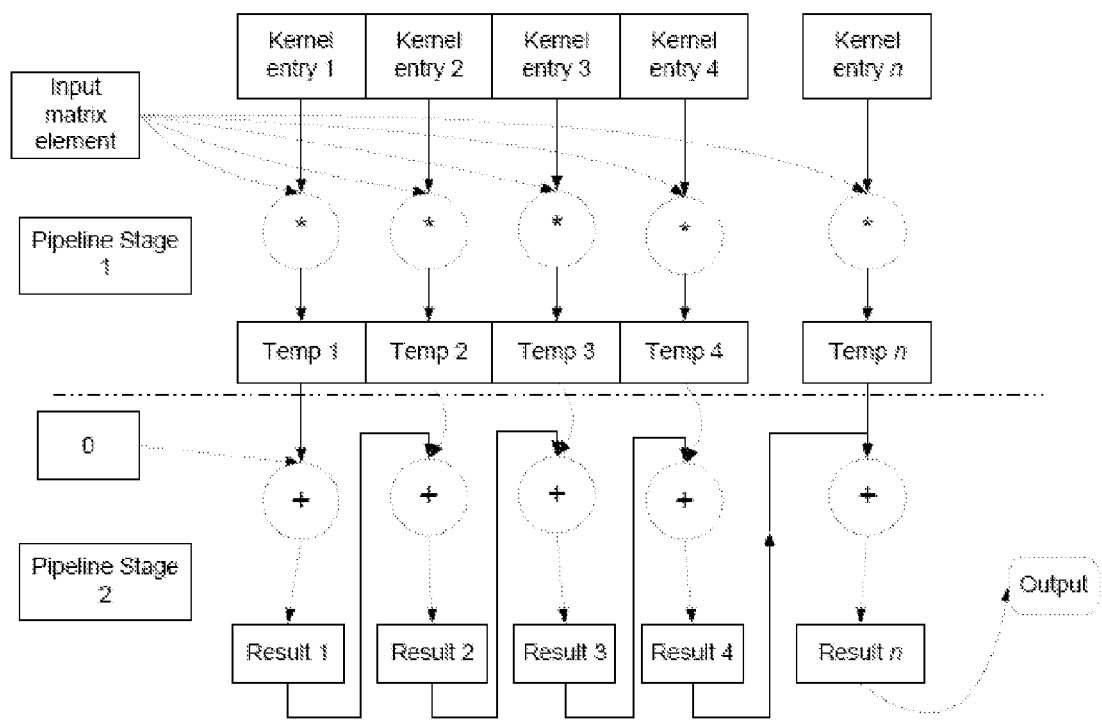
FIG. 14 is a flowchart of an example process of three-dimensional convolution using a one-dimensional convolver.

The approach to 3-D convolution described herein involves the repeated use of a single 1-D convolver. The 1-D convolver may be first used to compute a 2-D convolution. A number of 2-D convolutions may then be repeated to complete the entire 3-D convolution. FIG. 14 presents a picture of an example implementation for a 1-D convolver employed to compute 2-D and 3-D convolutions. In the illustrated example of FIG. 14, n represents the width of the convolution matrix. For a matrix of size m×n, there would be n individual convolution elements that would be used to compute the 2-D convolution. The algorithm for implementing a 1-D convolution can be seen in the algorithm presented in FIG. 15. Note that many of the operations in the algorithm may be performed in parallel and, in the hardware implementation of the algorithm, are performed in parallel. To give a clear presentation of the general idea, the steps are described sequentially below.

In addition to being able to calculate many different convolution results in parallel, the convolver is very efficient in terms of memory bandwidth. The convolver requires only one new matrix element every clock cycle, thus memory access latency can be completely masked by computation. Persons having ordinary skill in the art will appreciate that memory bandwidth, rather than computation power, are typically the bottlenecks encountered with convolvers.

Figure 16:
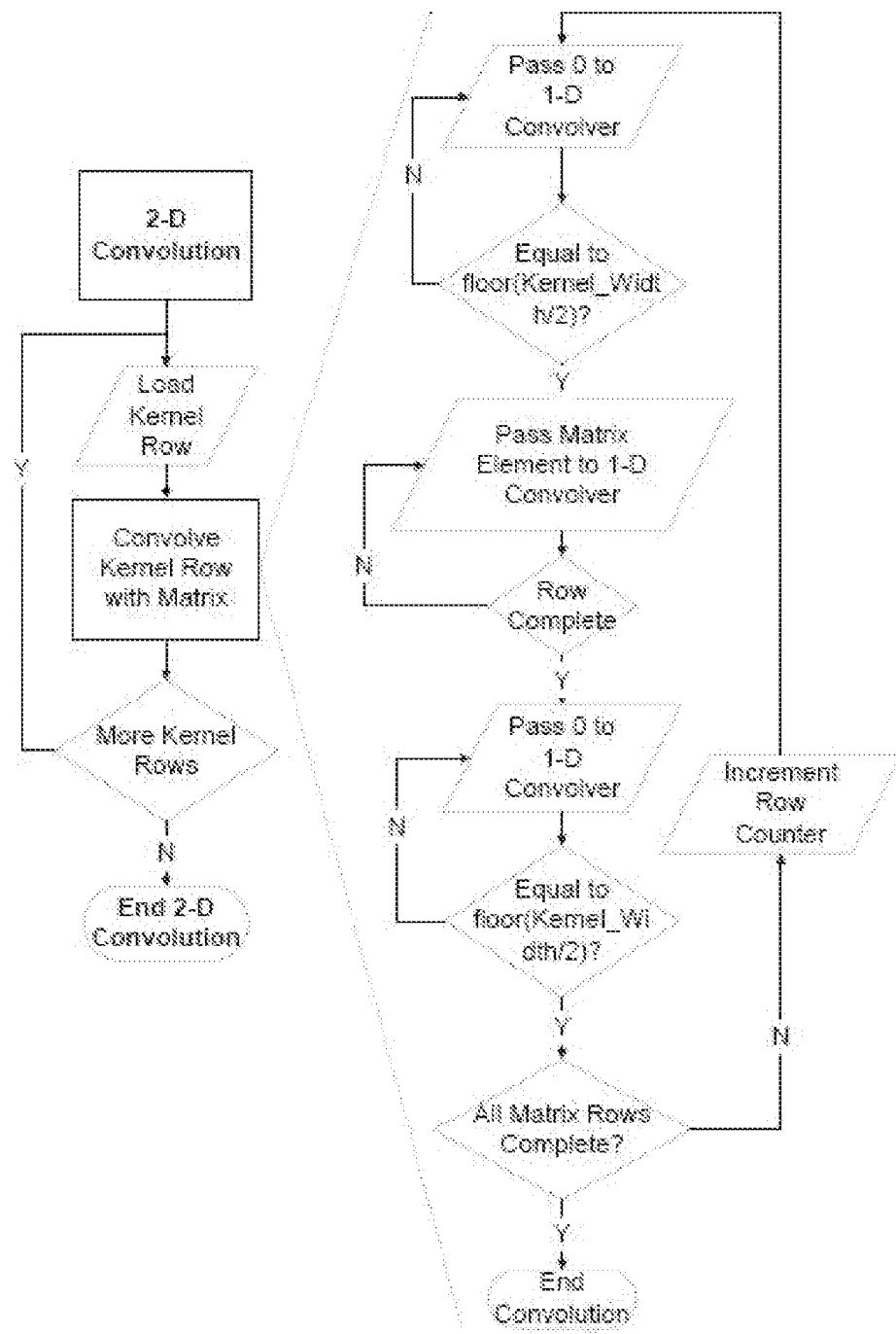
FIG. 16 is a flowchart of an example process of performing a two-dimensional convolution using a one-dimensional convolver.
Figure 17:
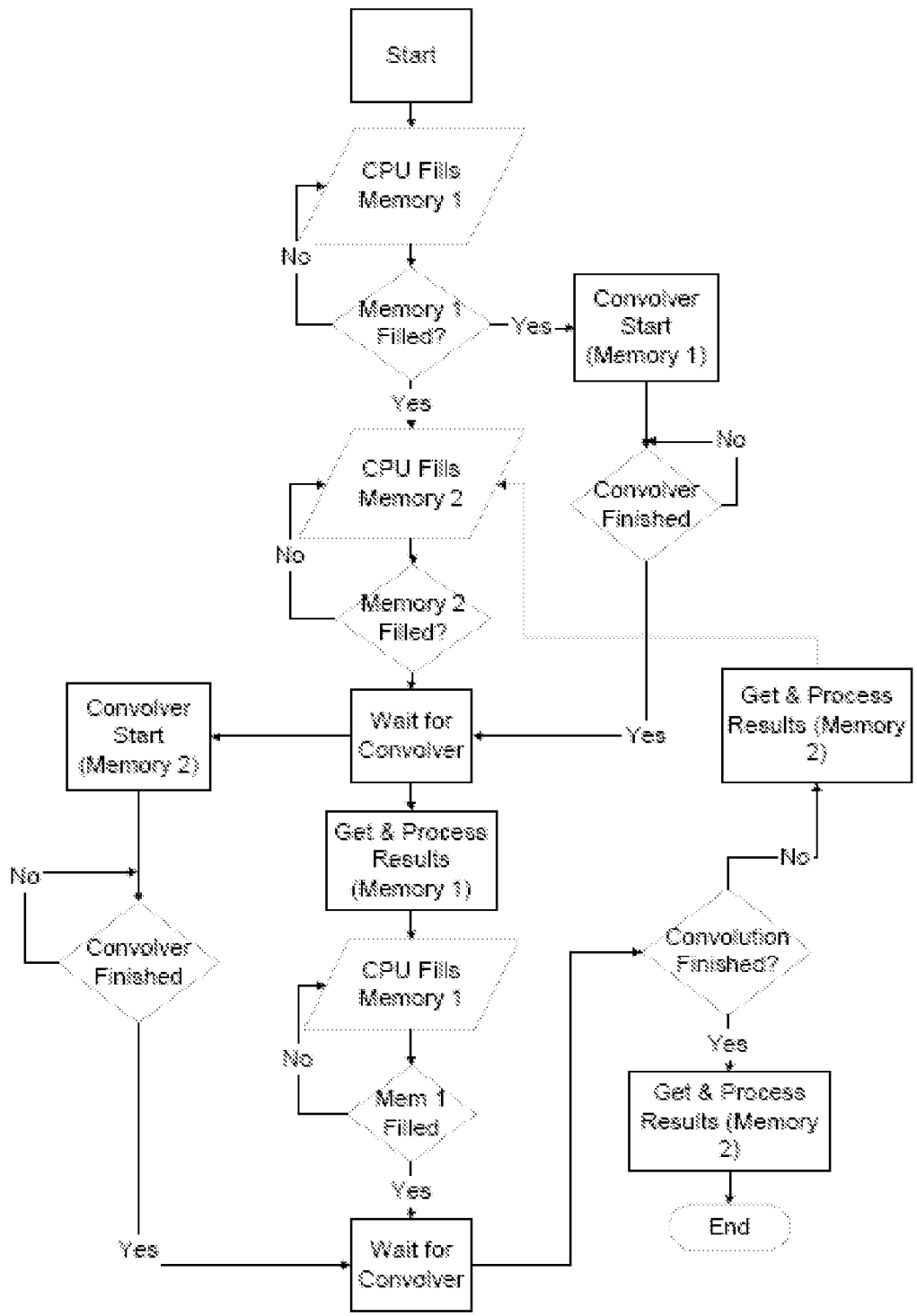
FIG. 17 is a flowchart of an example process of performing a three-dimensional convolution.

FIG. 16 illustrates an example method to take a 1-D convolver and create/calculate a 2-D convolution. However, to compute a 3-D convolution, a series of 2-D convolutions is used, as shown in the example method of FIG. 17. The number of 2-D convolutions needed is shown in Equation 14 below.

$$\text{num\_2d} = \qquad\qquad\text{Equation 14}$$

$$2 * \left(\left(1 + \left\lfloor\frac{n}{2}\right\rfloor * \left\lceil\frac{n}{2}\right\rceil + \frac{\left\lfloor\frac{n}{2}\right\rfloor}{2}\left(\left\lfloor\frac{n}{2}\right\rfloor + 1\right)\right) + n\left(N - 2\left(\left\lfloor\frac{n}{2}\right\rfloor + 1\right)\right)\right).$$

In Equation 14, n is used to represent kernel_depth, or the number of planes present in the convolution kernel, and N is used to represent convolution_depth, or the number of planes present in the convolution matrix.

Figure 18:
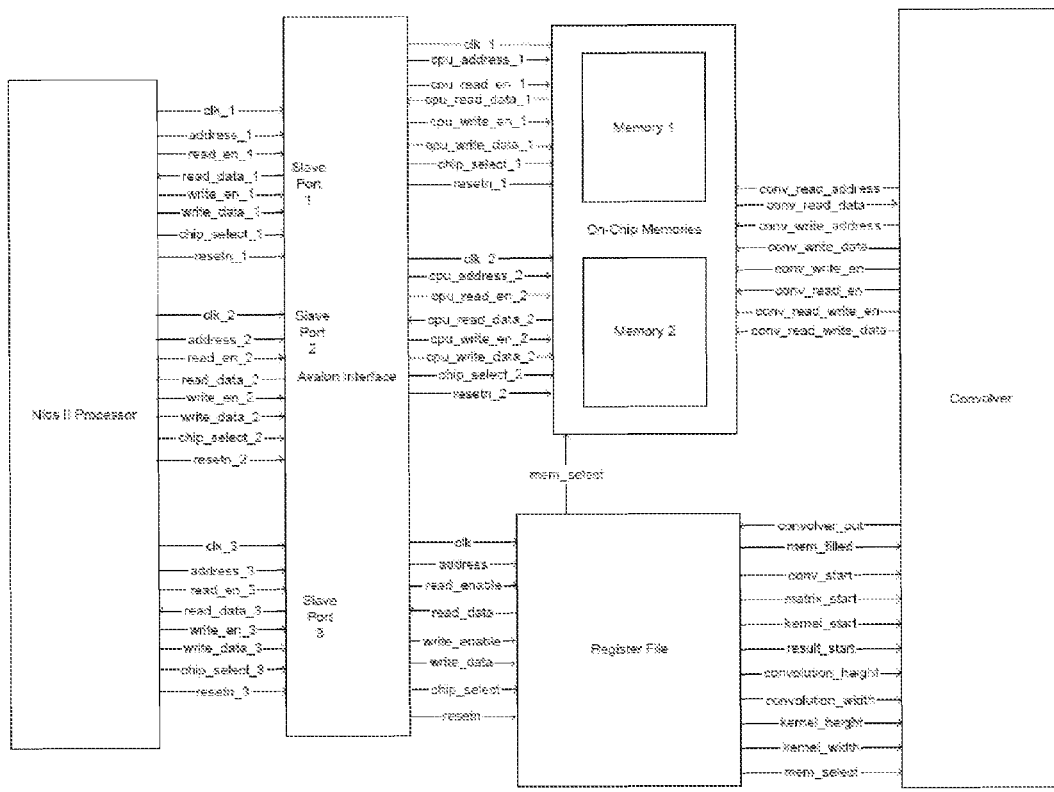
FIG. 18 is a block diagram of another example three-dimensional convolution system illustrating example communication and data signals.

A more detailed version of FIG. 12 is presented as FIG. 18. This figure provides additional information relating to example signals used and gives a more specific view of the implementation of the entire system.

Collapsed Cone

As mentioned earlier, the kernel used in an implementation using collapsed cone techniques is an exponentially calculated kernel. Along with the kernel, calculation of radiation dose may be realized when given an initial TERMA matrix in Cartesian coordinates. The exponentially calculated kernel is composed of at least two different components. One component calculates the primary energy (which has a rather sharp falloff as distance from the interaction point increases) and the other component calculates the scatter energy (which does not have near as sharp a drop-off as the primary energy). Equations to calculate the primary energy are shown below in Equations 15 and 16, and the equation to calculate the scatter energy is shown below as Equation 17.

$$\Delta R_{mn}^{p}(r_i) = T_i\rho_i\Omega_{mn}d^2u\int_{r_{i-1}}^{r_i}\frac{A_m}{a_m}e^{-a_m\eta_i(r_i-s)}ds = \qquad\text{Equation 15}$$

$$T_i\rho_i\Omega_{mn}d^2u\frac{A_m}{\eta_i a_m^2}(1-e^{a_m\eta_i\Delta r}).$$

$$R_{mn}^{p}(r_i) = R_{mn}^{p}(r_{i-1})e^{-a_m\eta_i\Delta r} + \Delta R_{mn}^{p}(r_i). \qquad\text{Equation 16}$$

$$R_{mn}^{s}(r_i) = R_{mn}^{s}(r_{i-1})(1 - b_m\eta_i\Delta r) + T_i\rho_i\Omega_{mn}d^2u\frac{B_n}{b_m}\Delta r. \qquad\text{Equation 17}$$

In the above equations, T represents the TERMA, $\rho_i$ represents the mass density, and $\eta_i$ represents the relative electron volume density of the segment i. Also, mn represents the current cone being calculated, and $d^2u$ represents a volume associated with the receiving voxel element. Equation 15 calculates the amount of primary energy released from the segment i, where r goes from $r_{i-1}$ to $r_i$, into the cone of solid angle $\Omega_{mn}$. Equation 16 represents the radiant primary energy through all segments on a line. Equation 17 is used to calculate the scatter energy. It does not explicitly require the exponentials because the scatter energy is only a small fraction of the total energy, hence the scatter energy can be approximated by the first two terms of the serial expansion. These equations serve to determine the amount of energy deposited in different voxels, which can then be used in calculating the final dose shown in Equation 18 below.

$$D(r) = \frac{\eta(r)}{\rho(r)}\frac{1}{d^2u}\sum_m\sum_n[a_m R_{mn}^{p}(r) + b_m R_{mn}^{s}(r)]. \qquad\text{Equation 18}$$

In Equation 18, $\eta(r)$ is divided by $\rho(r)$ to convert energy per voxel into dose per voxel. These equations allow computation of the dose in a phantom, provided values are given for the TERMA, the mass density, and the relative electron volume density. Suitable values for $A_m$, $a_m$, $B_m$, and $b_m$ are assumed to be available, and the value of $\Omega_{mn}$ may be calculated using Equation 19, shown below.

$$\Omega_{mn} = \frac{4*\pi}{\max\{mn\}}. \qquad\text{Equation 19}$$

In Equation 19, the $4\pi$ radians of the solid sphere are divided by the number of cones used. These equations serve to compute the dose, but may not be the best method for implementation in an FPGA. They involve a lattice of parallel lines which must be computed and laid out. Generally speaking, if there are 48 cones emanating from each dose calculation point ($\Delta\theta=3.75°$, $\Delta\Phi=360°$), then 48 different lattices would need to be constructed such that, for each lattice, no voxel was crossed by more than one line for that lattice. Additionally, for each line in the lattice, starting at the point where that line intersects with a voxel in the region of interest, Equations 15, 16, and 17 would be run. When these equations finished, the final dose could be calculated using Equation 18. Persons having ordinary skill in the art will appreciate that this lattice computation introduces additional calculations and hardware into the dose calculation phase, and use of the lattice does not allow for easy use of dose correction factors.

One of the correction factors this method does not easily allow for is kernel tilting, which allows for the computation kernel to be tilted in various ways to allow more accurate dose calculation(s). The calculation method described herein differs from that requiring the parallel lattice of lines described above. This is done for at least two different reasons. One main reason is that by using the lattice of lines, it is typically difficult to implement dose correction factors that would be required for a clinical implementation. Another reason is that Equations 15 and 16 require a constant $\Delta r$ to be used if accurate results are expected.

With the example interaction point of view implementation described herein, the cones are extended from each voxel with a nonzero TERMA value. TERMA indicates the energy released, and the kernel describes how that energy is dissipated from the interaction site. Therefore, if a voxel contains no TERMA, then there is no reason to ray-trace from it as there will be no energy deposited. FIG. 19 illustrates an example algorithm to describe how the primary energy distribution may be calculated. With the example algorithm of FIG. 19, there are more variables that must be tracked throughout the calculation. However, it enables a much more flexible implementation than Equations 15 and 16. In the illustrated example of FIG. 19, kernel tilting may be implemented by providing different $A_m$ and $a_m$, values. Persons having ordinary skill in the art will appreciate that similar methods may be used to handle kernel hardening and other dose correction factors.

As described above, Equations 15 and 16 require a constant $\Delta r$. Assuming $T_i$, $\rho_i$, $\Omega_{mn}$, $\eta_i$, $A_m$, and $a_m$ remain constant for each of these examples, then only $\Delta r$ may change. For example, assume that the original $\Delta r_1$ is large (e.g., $\Delta r_1\gg 1$)

and the second $\Delta r_2$ is small (e.g., $\Delta r_1 \ll 1$). As a result, the $(1-e^{-a_m \eta_i \Delta r})$ factor in Equation 15 is essentially $(1-e-\Delta r1)$ or ≈1. Accordingly, the initial $\Delta R^P_{mn}$ used to calculate $R^P_{mn}$ would be very large as most of the energy would have been deposited within the cone. The exponential factor in Equation 16 is meant as an attenuation factor, thus if $\Delta r_2$ is small, such that the exponential factor is ≈1, then nearly the same amount of energy will be deposited in the region of $\Delta r_2$ as was deposited in $\Delta r_1$, which is not sensible.

In another example, assume that $\Delta r_1$ is small and $\Delta r_2$ is large. In this case, almost the opposite effect occurs. Very little energy is released into the cone at $\Delta r_1$ as the exponential is ≈0, and then that small value is further attenuated for the large region when $\Delta r_2$ is used. Conceptually, a large amount of energy should be deposited in the region of $\Delta r_2$, however this is not true due to the use of different $\Delta r$'s.

Figure 20:
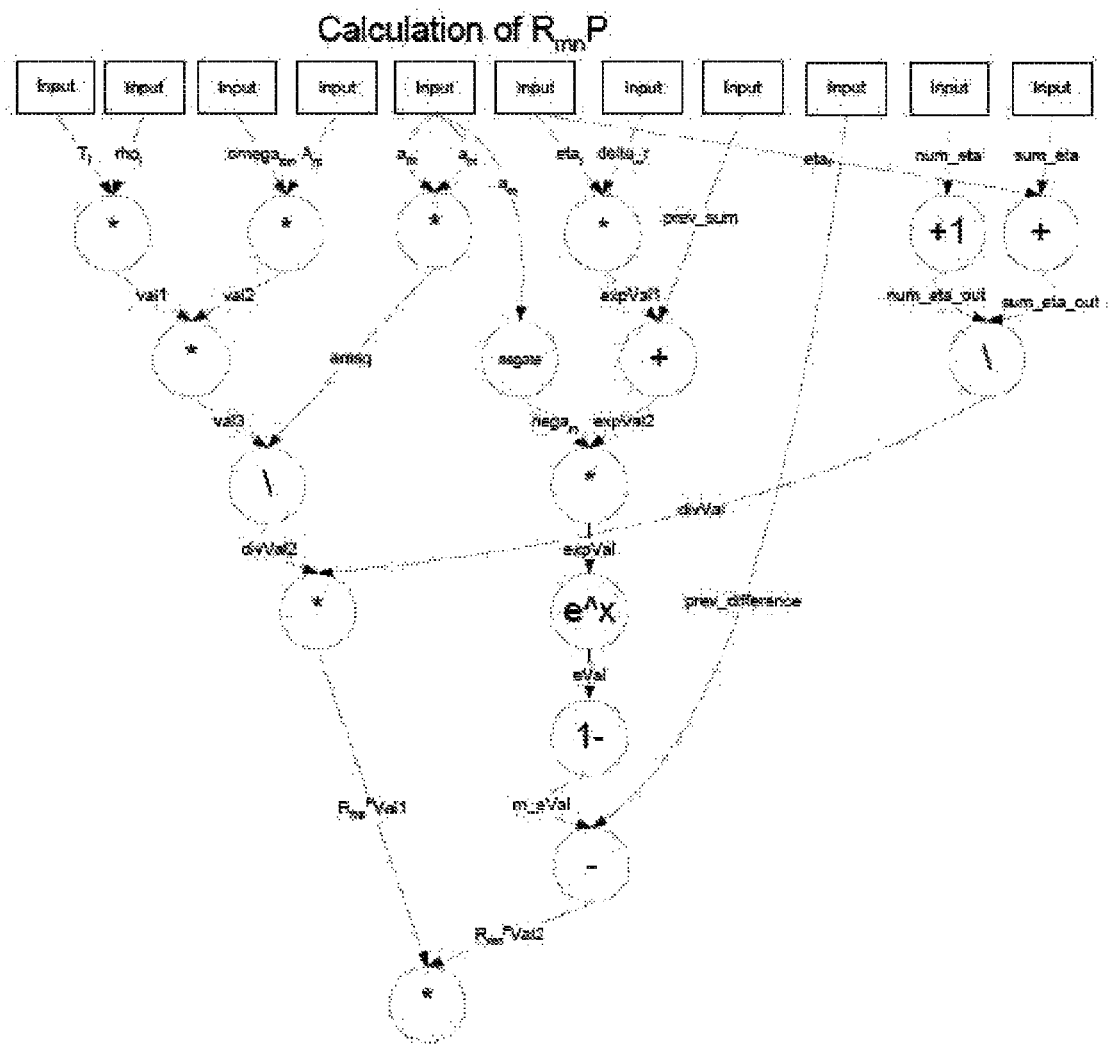
FIG. 20 is an example graph illustrating the process of calculating the primary energy distribution.

However, by using 2 $\Delta r$'s, $\Delta r_1$ and $\Delta r_2$ where $\Delta r_1 = \Delta r_2$, the equations will yield consistent results. That is, the same amount of energy will be deposited by Equations 15 and 16 as would be deposited by Equation 15 assuming that a $\Delta r_3$ was used where $\Delta r_3 = \Delta r_1 + \Delta r_2$. FIG. 20 illustrates a graph showing the processing of this function. The example graph of FIG. 20 shows initial inputs along with various steps required to produce an output. The function is fully pipelined and capable of producing a result every clock cycle after an initial period of latency.

Equation 17 was modified also to be equivalent to that of the algorithm presented in FIG. 19. The reason that Equation 17 was simpler than Equations 15 and 16 was due to the fact that scatter dose has less impact on the total dose than does the primary dose. However, in the case of dedicated hardware, because it is fully pipelined, it requires the same amount of time to compute the scatter dose using the complex or the simple method. Additionally, the more complex example method illustrated in the algorithm of FIG. 19 yields more accurate results than a potentially simpler implementation.

The calculations used in this collapse cone method require a $\Delta r$ value as shown in the algorithm presented in FIG. 19. This $\Delta r$ value is the length of the physical path that a ray travels through a particular voxel. The $\Delta r$ value may then be used to determine a radiological path length. Persons having ordinary skill in the art will appreciate that it is important to accurately calculate this physical path length, which is accomplished by the example methods and equations described below.

Ray-tracing includes determining the distance a line travels between a starting point and its first intersection with a voxel wall boundary. That is, given a starting point $\overrightarrow{position}$ and direction vector $\overrightarrow{direction}$, a line l is created originating at $\overrightarrow{position}$ and traveling to infinity in the direction described by $\overrightarrow{direction}$. Next, a determination is made as to which voxel wall boundary has been crossed first by 1. Calling this intersection point $\overrightarrow{INTERSECTION}$, it is then a simple calculation to determine the distance between the originating point $\overrightarrow{position}$ and the intersection point $\overrightarrow{INTERSECTION}$. Discussed in further detail below are example equations used in this ray-tracing calculation, and a description of its pipelined implementation in hardware.

To calculate a path length, there must be some values which are available at the beginning of the calculation. The following include some required values and provide a description of the function each example value serves. $\overrightarrow{voxel\_size}$, for example, describes the size of each voxel in the x, y, and z directions. Additionally, the value offset describes the x, y, and z offsets of voxel numbers. $\overrightarrow{position}$ describes a vector representing the current position of the interaction site, and $\overrightarrow{direction}$ describes a vector representing the direction the photon was traveling.

At least one of the initial values is $\overrightarrow{position}$, thus if the point of intersection with a voxel wall boundary can be calculated, then it is a simple task to compute distance. Determining the current voxel in which the ray is positioned may be accomplished by using the initial position and the knowledge that the center top point of the matrix has a location of (0, 0, 0). Equations 20, 21, and 22 present example calculations for this step.

$$\text{voxels\_x} = \begin{cases} \dfrac{postion.x}{voxel\_size.x} - 1/2 & \text{if } position.x \geq 0 \\ \dfrac{position.x}{voxel\_size.x} + 1/2 & \text{otherwise} \end{cases} \quad \text{Equation 20}$$

$$\text{voxels\_y} = \begin{cases} \dfrac{postion.y}{voxel\_size.y} - 1/2 & \text{if } position.y \geq 0 \\ \dfrac{position.y}{voxel\_size.y} + 1/2 & \text{otherwise} \end{cases} \quad \text{Equation 21}$$

$$\text{voxels\_z} = \dfrac{postion.z}{voxel\_size.z}. \quad \text{Equation 22}$$

The current voxel may be taken to be [voxels_x+offset_x, voxels_y+offset_y, voxels_z+offset_z]. After determining the current voxel location, the locations of the boundary walls for this voxel are determined. Even though there are six boundary walls, only three of them are of particular interest due to x, y, and z having either a positive or negative direction. Example calculations used to determine the boundary planes are shown below as Equations 23a, 23b, 24a, 24b, 25a, and 25b.

$$x_0 = \begin{cases} \left(\text{voxels\_x} * \text{voxel\_size}.x + \dfrac{\text{voxel\_size}.x}{2}\right) & \text{if } direction.x \geq 0 \\ \left(\text{voxels\_x} * \text{voxel\_size}.x + \dfrac{\text{voxel\_size}.x}{2}\right) & \text{otherwise} \end{cases} \quad \text{Equation 23}$$

$$y_0 = \begin{cases} \left(\text{voxels\_y} * \text{voxel\_size.}y + \dfrac{\text{voxel\_size.}y}{2}\right) & \text{if } direction.y \geq 0 \\ \left(\text{voxels\_y} * \text{voxel\_size.}y + \dfrac{\text{voxel\_size.}y}{2}\right) & \text{otherwise} \end{cases}$$ Equation 24

$$z_0 = \begin{cases} (\text{voxels\_z} * \text{voxel\_size.}z + \text{voxel\_size.}z) & \text{if } direction.z \geq 0 \\ (\text{voxels\_z} * \text{voxel\_size.}z) & \text{otherwise} \end{cases}$$ Equation 25

Examination of the direction vector and position vector, and either adding or subtracting voxel_size for the appropriate direction, allow verification that $x_0$, $y_0$, or $z_0$ fall exactly on the boundary of the voxel. In that case, the boundary of the next voxel may be examined instead of the current one. After determining the boundaries for the x, y, and z directions, a determination may be made regarding where the rays crossed on each of these planes. Equation 26 shows an example calculation for determining the amount of "time" taken before the plane for the x direction is crossed. Calculations for the y and z directions are similar. The boundary crossed is indicated by min{cross_x, cross_y, cross_z} and is designated p_c. Using this information, Equations 27, 28, and 29 show example calculations for determining the actual point at which the ray crossed the voxel boundary. The distance is calculated using Equation 30.

$$\text{cross\_x} = \dfrac{|x_0 - position.x|}{|direction.x|}.$$ Equation 26

$$\text{cross\_pt.}x = \begin{cases} position.x + direction.x * \text{p\_c} & \text{if } \text{p\_c} \neq \text{cross\_x} \\ x_0 & \text{otherwise} \end{cases}$$ Equation 27

$$\text{cross\_pt.}y = \begin{cases} position.y + direction.y * \text{p\_c} & \text{if } \text{p\_c} \neq \text{cross\_y} \\ y_0 & \text{otherwise} \end{cases}$$ Equation 28

$$\text{cross\_pt.}z = \begin{cases} position.z + direction.z * \text{p\_c} & \text{if } \text{p\_c} \neq \text{cross\_z} \\ z_0 & \text{otherwise} \end{cases}$$ Equation 29

$$\begin{aligned} dx &= (\text{cross\_pt.}x - position.x)^2 \\ dy &= (\text{cross\_pt.}y - position.y)^2 \\ dz &= (\text{cross\_pt.}z - position.z)^2 \\ \text{distance} &= \sqrt{dx + dy + dz}. \end{aligned}$$ Equation 30

Figure 21:
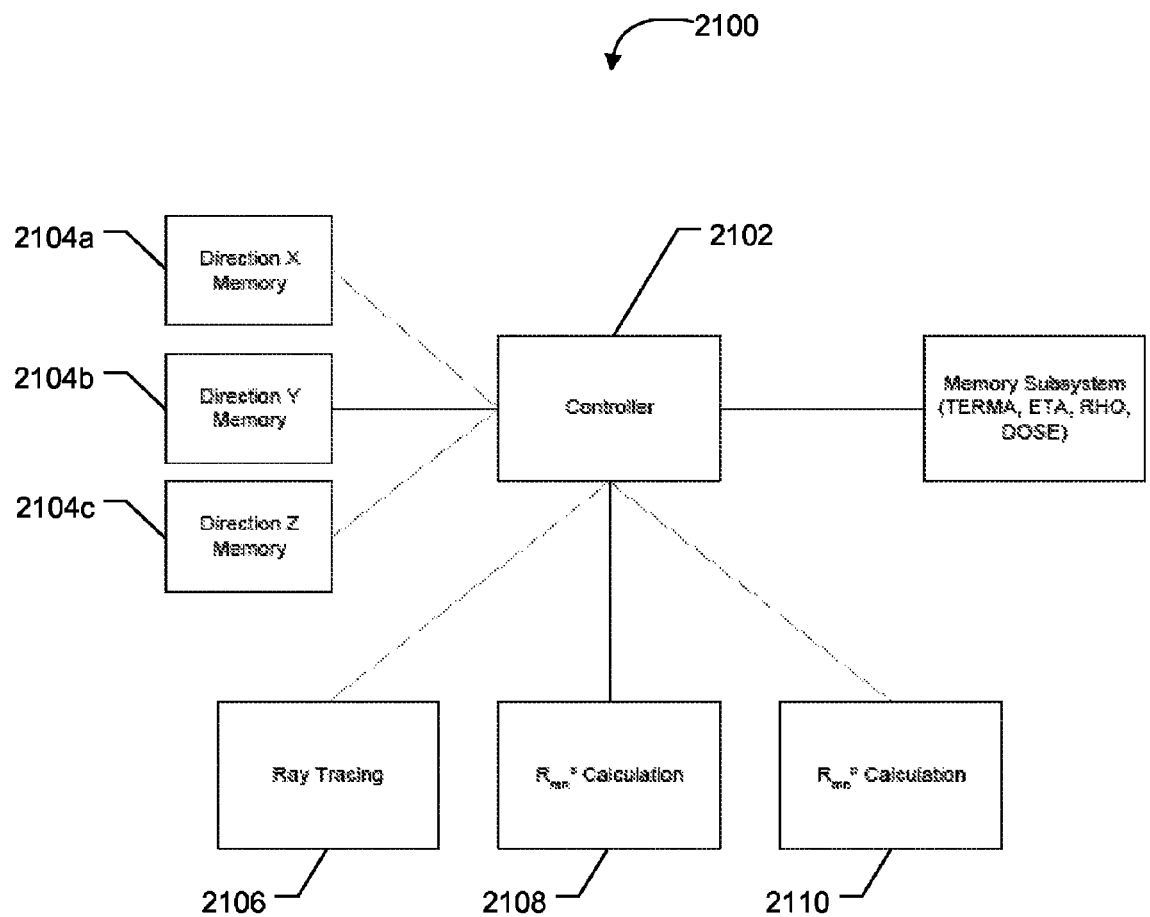
FIG. 21 is a block diagram of an example collapse cone system.

FIG. 21 illustrates an example system that may be employed to implement the Collapsed Cone process. In the illustrated example system 2100 of FIG. 21, a controller 2102 marshals communication with each of the individual components. Memory locations 2104a, 2104b, and 2104c are initialized with the required data prior to start of the calculation, and Table 8 illustrates example memory locations at which different values are placed. The example system 2100 also includes a ray-tracer 2106, a primary energy calculator 2108, and a scatter energy calculator 2110. Some of these values may be calculated (using various supplied values) by the FPGA, but to decrease the area usage and time requirements of the FPGA, they may be preloaded into memory.

TABLE 8

Parameters and Initial Memory Locations

| Variable Name | Initial Location |
|---|---|
| matrix dimensions | 0 |
| voxel size | 6 |
| $\Omega_{mn}$ | 9 |
| $A_m$ | 10 |
| $a_m$ | 58 |
| $B_m$ | 106 |
| $b_m$ | 154 |
| region of interest | 203 |
| number of cones | 209 |
| offset | 210 |
| voxel size/2 | 213 |
| number $\Phi$ | 216 |
| TERMA | 300 |
| $\eta$ | 1,000,300 |
| $\rho$ | 2,000,300 |
| dose output | 3,000,300 |
| direction vectors | 4,000,300 |

Most of the values are used in the $R^P_{mn}$ or $R^s_{mn}$ calculations discussed above. Some of the other values, such as the direction vectors and voxel sizes, are typically used in the ray-tracing calculations.

Convolution and Collapsed Cone Analysis

Implementation of the direct convolution system and the collapse cone include various hardware design languages including, but not limited to, software packages from ALTERA® and CELOXICA®. However, persons having ordinary skill in the art will appreciate that other software packages and/or hardware may be implemented to employ the methods and apparatus described herein, without limitation.

The HANDEL-C® design language by CELOXICA® was used in the construction of many components to implement, for example, the main convolver and the direct convolution system. The collapse cone system also made use of a channel object provided by CELOXICA®. Channels were used in the collapse cone system to communicate between different objects. Channels are an object provided in HANDEL-C® to synchronize processing and communicate across object and clock domains. In the case of the system described herein, there is only one example clock domain, but persons having ordinary skill in the art will appreciate that different components could be moved into different clock domains for processing. Using channels, it is a fairly simple task to synchronize the communication between all of the different components and ensure correct functionality.

The example collapsed cone algorithm uses IEEE-754 floating point arithmetic. As discussed above, there has been a lot of work in the industry in the area of floating point processing on FPGAs. Such work allows for many different floating point libraries available for use. In the illustrated example methods and apparatus described herein, a floating point library was selected that is provided by CELOXICA® as part of their Platform Developers Kit (PDK). This library may afford efficient implementation and allow relative ease of integration within HANDEL-C® code. A list of example pipelined floating point functions provided by the PDK is shown in Table 9. All functions presented take as input, and produce as output, IEEE 32-bit floating point numbers.

TABLE 9

Floating Point Functions Provided By CELOXICA ®

| Function Name | Description |
| --- | --- |
| FloatPipeAdd | Add two floating point numbers |
| FloatPipeMultiply | Multiply two floating point numbers |
| FloatPipeDiv | Divide two floating point numbers |
| FloatPipeSub | Subtract two floating point numbers |
| FloatPipeSqrt | Take the square-root of a floating point number |
| FloatPipeEq | Perform equality test |
| FloatPipeGt | Perform greater-than comparison |
| FloatPipeLs | Perform less-than comparison |

In the illustrated Table 9, each function listed requires a specific number of clock cycles before returning a result. The number of cycles may be determined by taking the function name and adding the word Cycles to it, i.e., FloatPipeAdd requires FloatPipeAddCycles of latency before producing an initial result.

Another design language used in the construction of these systems includes VHDL (VHSIC Hardware Description Language). All components of the direct convolution system (except for the convolver itself) have been written in VHDL. Additionally, the VHDL version of the NIOS processor provided by Altera was used in the example methods and apparatus described herein. For the collapse cone system, only the high level module combining the components was written in VHDL.

SOPC Builder by ALTERA® was used to connect all of the components of the direct convolution system together. Components that were unneeded (such as the 7-segment display) were removed and a new convolver component was constructed. This new component included the embedded memories, the register file, and the convolver itself. It was combined with the NIOS II® processor using three different slave ports. Two of these slave ports were used by the NIOS II® processor solely to communicate with the embedded memories (only one was allowed to be used at a time), while the other port was used to communicate with the register file. Connections between the register file, the embedded memories and the convolver were coded in VHDL prior to combining them into a component.

In the illustrated examples, communication between the NIOS II® processor and the direct convolution system was accomplished via the AVALON® interface created by ALTERA®. It can account for wait states, different clock domains, and inherently handles bus arbitration between master and slave peripherals.

Figure 22:
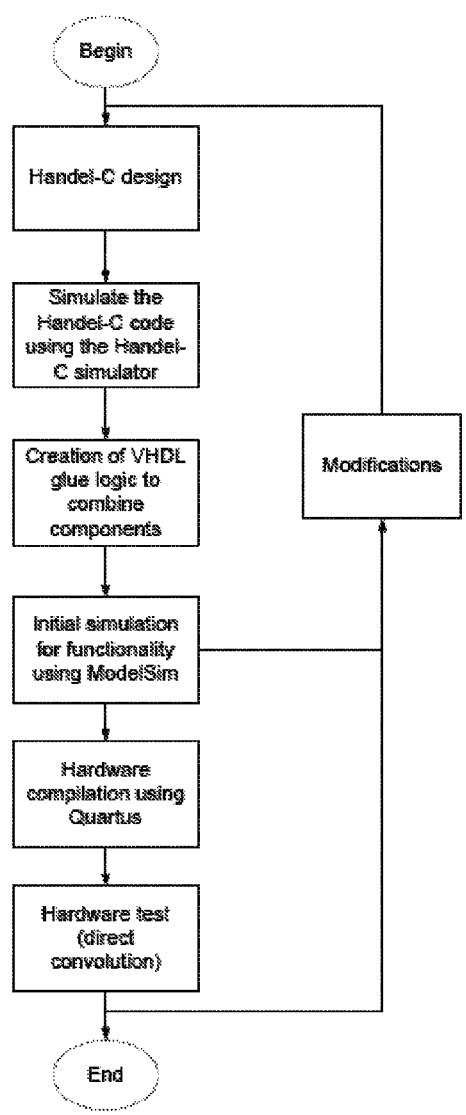
FIG. 22 is a flowchart of an example process to design dose calculation systems.

Described herein are results and analysis related to the performance and accuracy of example methods of dose calculation. The design flow used for the creation and testing of these designs is shown in FIG. 22, which illustrates various languages used along with the simulation and compilation stages. All of the example direct convolution designs were run on an ALTERA® development board featuring a STRATIX® EP1S40 chip, but persons having ordinary skill in the art will appreciate that other chips may be employed. The designs were compiled using the QUARTUS II® software version 5.0. Different levels of fitter effort and goals were used at different times as described below.

The convolution subsystem runs at the same speed as the NIOS II® processor on the STRATIX® chip. Accordingly, multiple clock domains may be avoided, which would otherwise necessitate additional testing and precautions. Persons having ordinary skill in the art will appreciate that future clocks of higher speed may operate with the example convolver without limitation. The timing requirements for the clock of the convolution system were set to a minimum of 50 MHz. The compilation was for a 25 element convolver and allowed the convolution system to run at 52.28 MHz, utilizing 18,529 LEs (Logic Elements), all 112 available DSP blocks, and 1,920,000 on-chip memory bits. With maximum fitter effort, the compilation took 5 times longer and yielded a new maximum clock frequency was 57.76 MHz and used 20,889 LEs. The usage of other components remained the same.

The equations used to determine the amount of time needed (in terms of clock cycles) to perform a single 2-D convolution using the constructed convolver include:

A time per convolution element (element_time), which consumes 2 clock cycles, and a number of convolution elements (num_element), which equals conv_height*(conv_width+2[kernel_width/2])* kernel_height. Additionally, a time between convolution rows (time_conv_row) consumes 3 clock cycles, and a number of rows (num_rows) equals cony height*kernel_rows. A time between kernel rows (time_kernel_row) consumes 15 clock cycles, a time to load kernel_row (time_load) consumes the same amount of clock cycles as kernel_width, and a time after load of kernel row before the convolution starts (time_after) consumes 13 clock cycles. Variables used are further explained in Table 10.

TABLE 10

Variables Used in the Convolution Speed Calculation

| Variable Name | Description |
| --- | --- |
| conv_height | Number of rows in the convolution matrix |
| conv_width | Number of columns in the convolution matrix |
| kernel_height | Number of rows in the kernel matrix |
| kernel_width | Number of columns in the kernel matrix |

The total time to perform a single 2-D convolution can be estimated by Equation 31, which helps to enable further optimization. It enables evaluation of the different amounts of time needed by various parts of the calculation.

$$Convolution\_Time = element\_time * num\_elements + time\_conv\_row * num\_rows + (time\_load + time\_kernel\_row + time\_after) * kernel\_rows. \quad \text{Equation 31}$$

Table 11 illustrates times obtained using these example calculations, which closely match those obtained by simulation. The simulation results are obtained by using ModelSim with the correctly sized matrix and kernel.

TABLE 11

Time Difference Between Simulated and Calculated Convolution Times

| Matrix Size | Kernel Size | Sim. Cycles | Calc. Cycles | % Diff. |
| --- | --- | --- | --- | --- |
| 10x10 | 5x5 | 1,682 | 1,715 | 1.96% |
| 20x20 | 10x10 | 12,784 | 12,990 | 1.61% |
| 100x100 | 100x100 | 4,032,601 | 4,042,800 | 0.25% |

In addition to using the FPGA board to perform the convolution, the same 2-D convolution was performed using a computer. The specifications for the computer are shown in Table 12. Comparisons of the running time between the computer and the FGPA board are shown in Table 13. The results illustrate that the larger the overall convolution is, the more speedup the FPGA may be able to obtain over the computer. For example, a matrix of size 10×10 and a kernel of size 5×5 results in an FPGA speedup of 1.56× over the computer, but with a matrix and kernel each of size 100×100, the FPGA can achieve a speedup of ≈218×. This additional speedup with the larger matrices is typically due to the increased size of the 1-D convolver, which illustrates that more operations are performed in parallel.

TABLE 12

Specifications for Host PC

| Component | Description |
|---|---|
| CPU | Intel Pentium M 1.4 GHz |
| Memory | 512 MB in 2-256 MB DIMM modules |
| Hard Drive | Fujitsu 40 GB, 5400 RPM |
| Graphics Card | NVIDIA 64 MB |
| Ethernet | 10/100 Ethernet card |

TABLE 13

Specifications for Host PC

| Matrix Size | Kernel Size | FPGA Time | Computer Time | Speedup |
|---|---|---|---|---|
| 10×10 | 5×5 | 33,640 ns | 52,580 ns | 1.56 |
| 20×20 | 10×10 | 255,680 ns | 788,100 ns | 3.08 |
| 100×100 | 100×100 | 80,652,000 ns | 17,648,070,000 ns | 218.82 |

Using Equation 9 to determine the required number of 2-D convolutions, the amount of time needed by the FPGA is extrapolated to perform a 3-D convolution. The results of this are shown in Table 14.

TABLE 14

3-D Convolution Times Using Repeated 2-D Convolutions

| Matrix Size | Kernel Size | # 2-D Convolutions | 3-D Conv. Time |
|---|---|---|---|
| 10×10 | 5×5 | 44 | 1,480,160 ns |
| 20×20 | 10×10 | 170 | 43,465,600 ns |
| 100×100 | 100×100 | 7450 | 600.8574 s |

Additionally, the information shown in Table 15 shows a comparison of using the FPGA, with the extrapolated data to perform a 3-D convolution compared to using a computer. As with the 2-D convolution comparisons, it can be seen that as the size of the overall convolution grows, so does the advantage of using the FPGA over the computer.

TABLE 15

Comparison of Estimated 3-D Convolution Times with those of a CPU

| Matrix Size | Kernel Size | FPGA Time | CPU Time | Speedup |
|---|---|---|---|---|
| 10×10 | 5×5 | 1,480,160 ns | 3,070,000 ns | 2.074 |
| 20×20 | 10×10 | 43,465,600 ns | 188,241,000 ns | 4.331 |
| 100×100 | 100×100 | 600.8574 s | 21,103.916 s | 35.12 |

While the speedup over the computer is only ≈2× for the smallest convolution, it rises to ≈35× for the largest convolution performed. This is a substantial improvement over the computer implementation.

To test the correct functioning of the convolution system on hardware and/or simulation, the design was compiled for and executed on the NIOS II® Development Kit, STRATIX® Professional Edition development board. For this example board, the 100×100 convolver cannot fit on the FPGA chip due to the amount of multipliers needed for the convolver. However, a 100×100 convolver was able to be compiled for a larger chip, the STRATIX® EP1S80.

Figure 23:
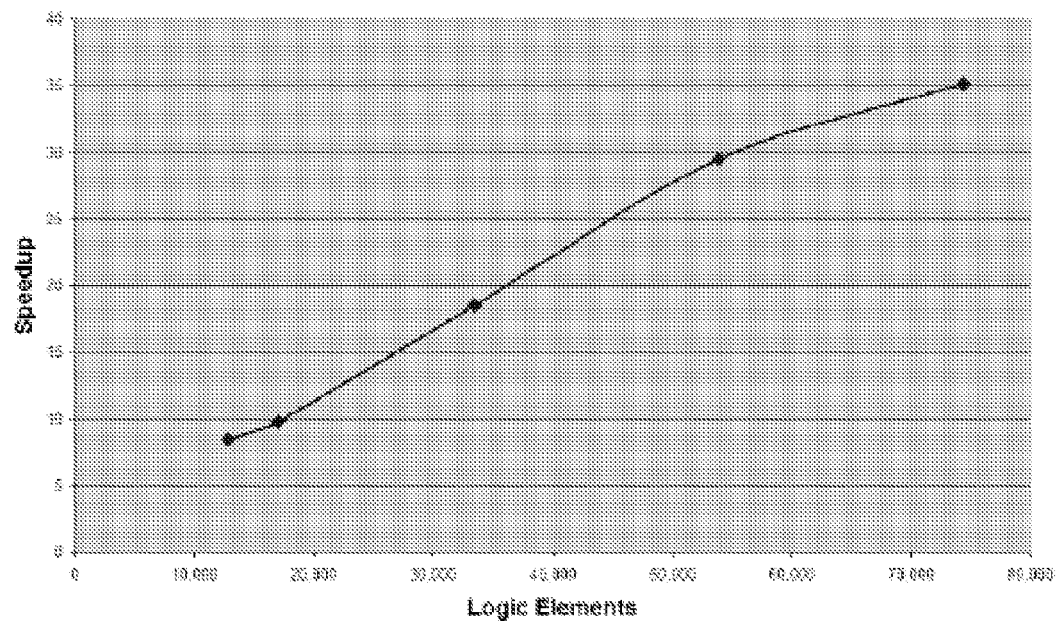
FIG. 23 is an example plot comparing a speed change based on a number of logic elements used.

In addition to comparing the speedup between the hardware and software convolution systems for specific sizes of convolvers, the speedup of the system was also compared in terms of logic elements used. QUARTUS® was used to compile the system for different sizes of convolvers and the number of logic elements used was compared against the speedup of the system. These results are shown in FIG. 23. It can be seen that the speedup is nearly linear with the increase in processing elements.

The example hardware design for this algorithm may handle one new input every clock cycle. Persons having ordinary skill in the art will appreciate that the development board is used for demonstrative purposes and has limited memory bandwidth. For each calculation performed there are 5 different values that must be obtained from memory. Given that the only memories available from the board are one SDRAM memory bank of 32 MB, and one SRAM bank of 1 MB, it is infeasible to expect that all 5 values could be obtained in one clock cycle. However, running the memory at twice the speed of the convolution system may allow buffering of data. In this manner, the delay for accessing data values could decrease from a maximum of 5 clock cycles to 2 cycles for performing a calculation.

Table 16 presents the total number of cycles required for the calculation of components used in this system. As each component is fully pipelined, the given latency can be masked by computation. Additionally, as the size of the overall calculation grows, this initial latency becomes negligible.

TABLE 16

Cycles Required for Computation of Different Components

| Component | Number of Cycles |
|---|---|
| Exponential calculation | 110 |
| $R^p_{mn}$ | 163 |
| $R^s_{mn}$ | 163 |
| Ray-Tracing | 212 |
| Entire Calculation | 428 |

For the row of the table representing the entire calculation, it should be noted that memory latency is ignored. It is assumed that data is available as it is needed. In reality, the data is typically obtained from memory with some delay, and that delay may be included in the final computation results. Also, the calculation of $R^p_{mn}$ and $R^s_{mn}$, usually uses an exponential function that requires the number of cycles reported. The actual number of cycles required for $R^p_{mn}$ and $R^s_{mn}$ may be calculated by subtracting the number given from the cycles required for the exponential calculation.

Figure 24:
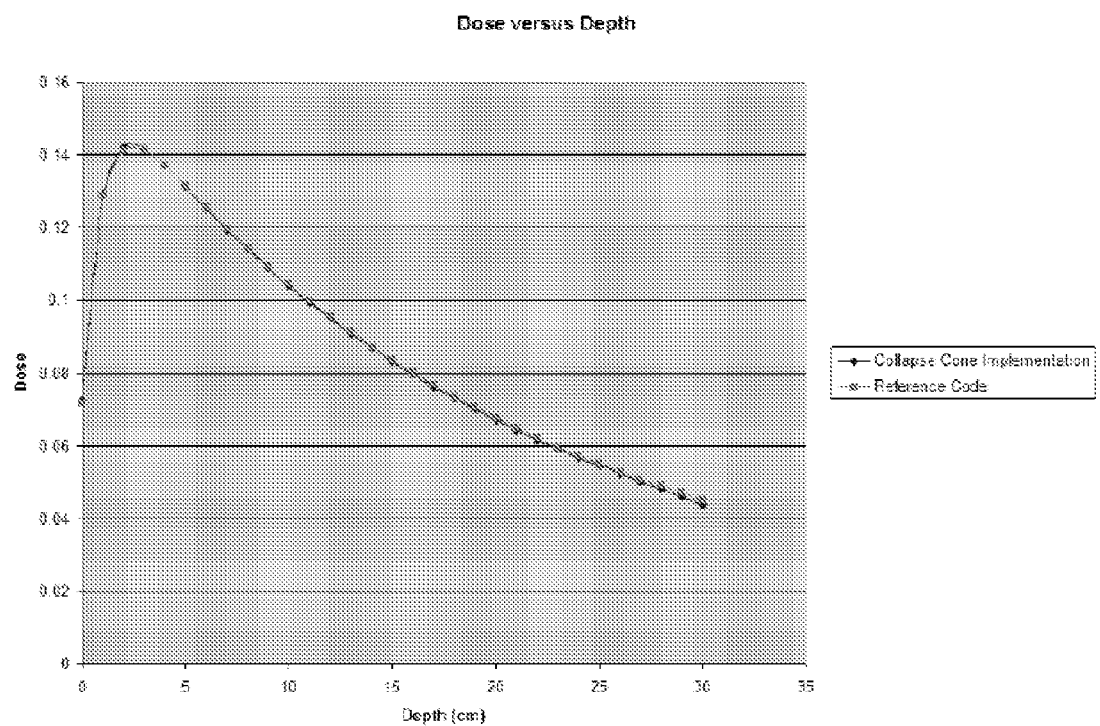
FIG. 24 is an example plot comparing dose calculations between reference code and a collapse cone implementation.

A software implementation of the collapse cone algorithm has been developed and compared with dose calculation software. In the example test case used, the developed software algorithm has a maximum off-axis error of 5.83% and an average error of only 1.15% compared to the dose calculation software. FIG. 24 presents a graph comparing the software collapse cone implementation results with the dose calculation reference code. The results are presented for the center axis of the phantom and show very close agreement between the two implementations. Due to the near overlapping of the lines in FIG. 24, the software was judged to be correctly implemented.

The hardware created performs exactly the same calculation as the collapse cone software, which employs 32-bit floating point operations, and were used in the C++ software created, as well as in the Celoxica floating point functions provided. In this way it was easy to check the accuracy of the hardware and to determine whether or not the final calculation was correct. The number of times the calculation was performed has been taken from the software implementation.

Presented in Table 17 are the results of using the collapse cone hardware and software. The number of cones computed for each voxel directly affects the number of calculations.

TABLE 17

Calculation Times for Hardware and Software Collapse Cone Implementation

| # of Cones | # Calculations | Software Time (s) | Hardware Time (s) | Ave. time/ calc (ns) for SW | Ave time/ calc (ns) for HW |
|---|---|---|---|---|---|
| 48 | 7,655,573 | 7.2 | 0.306 | 940.49 | 40 |
| 384 | 70,909,088 | 67.79 | 2.836 | 956.01 | 40 |
| 1152 | 209,969,888 | 209.52 | 8.399 | 997.86 | 40 |

If the number of cones increases by a factor of 2, the number of calculations increases proportionally. There is not an exact doubling due to differences in the number of voxels encountered during ray-tracing. The number of cones is calculated as the number of radial divisions multiplied by the number of azimuthal divisions ($\Delta\Phi$). The table presents how the number of calculations varies depending on the number of cones. It can be seen that the hardware is much more efficient at performing this calculation than the software implementation.

To compute the required amount of time for the hardware implementation, simulation data was used. Ignoring initial latency, it requires 2 cycles to complete a result. Therefore, to obtain the hardware calculation time, a clock cycle rate of 20 ns was chosen (50 MHz) and final calculation time was based on that clock rate. The individual components (ray-tracing, $R^p_{mn}$ and $R^s_{mn}$) have been compiled using the QUARTUS® software for the STRATIX® EP1S40 chip on currently available development boards. These components were able to achieve a cycle time of 10 us (100 MHz). As the STRATIX II® chip on the new development board is both larger and faster than current STRATIX® chip, once the components are combined, a cycle rate of 20 ns may result. The total time for the hardware is shown in Equation 32. For the size of the calculations performed (the smallest requires 7 million computations) the setup time along with initial and final latency are negligible.

$$t = SetupTime + InitLatency + \frac{Num\_Calculations}{Frequency} + FinalLatency.$$

Equation 32

Figure 25:
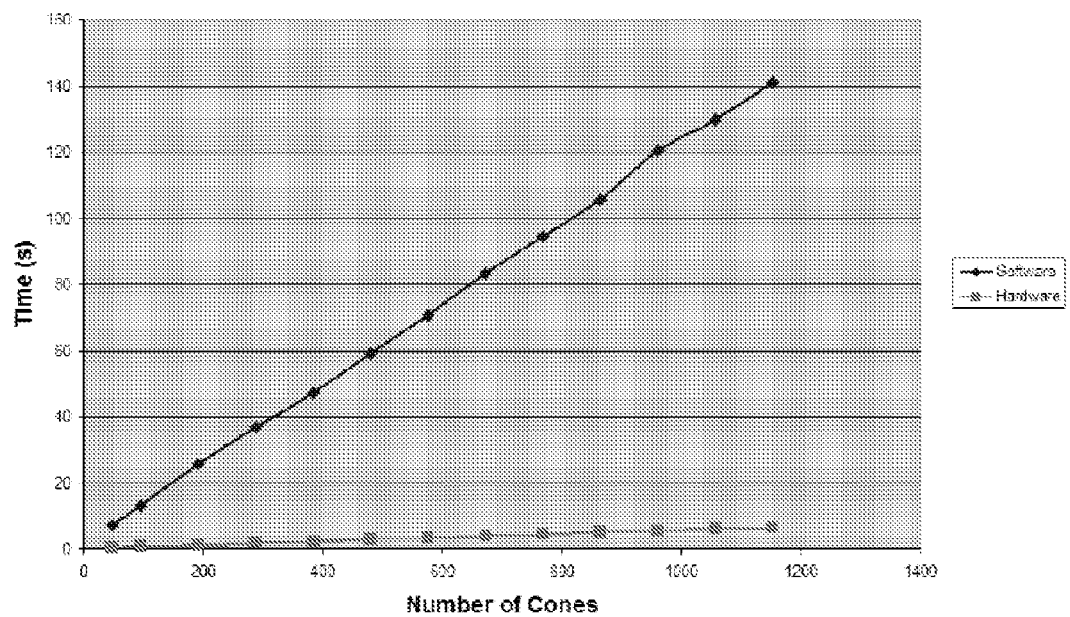
FIG. 25 is an example plot comparing required time for a collapse cone implementation based on the number of cones used.
Figure 26:
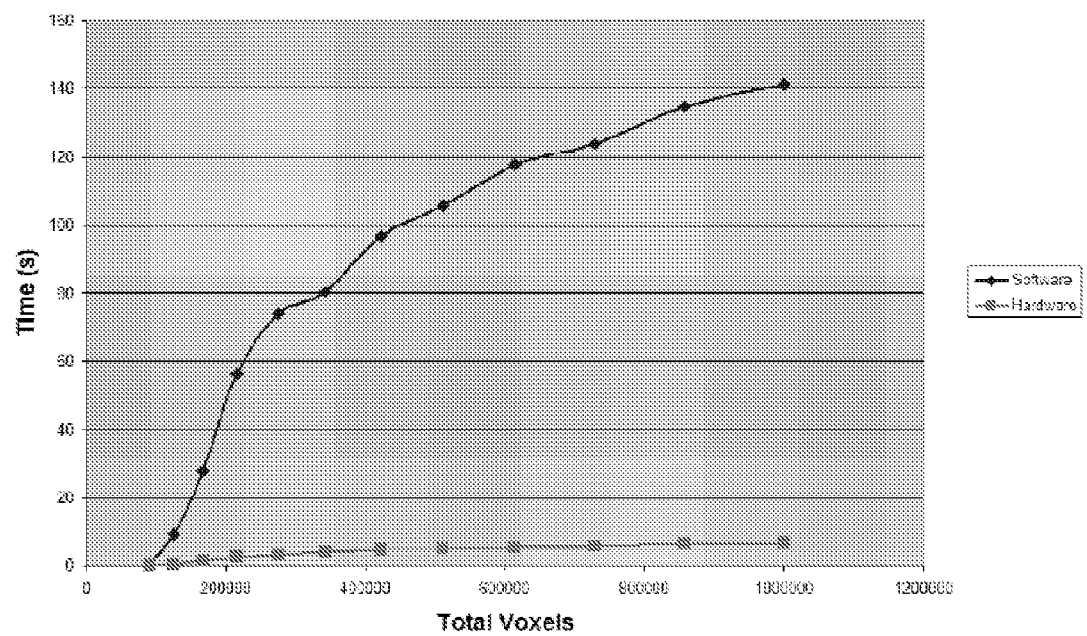
FIG. 26 is an example plot comparing required time for a collapsed cone implementation on hardware versus software.

As noted in Table 17, the computation time varies with the number of cones, as shown graphically in FIG. 25. Additionally, the computation time varies as the size of the matrix changes. When the matrix is larger, there are typically more voxels that must be ray-traced through, and more voxels where dose is deposited. FIG. 26 shows the impact that changing the matrix size has on the computation time. The x-axis lists total number of voxels and the graph illustrates how changing the number of voxels results in increased computation time.

A software based dose calculation includes a dose deposition point of view, where the dose is only calculated for voxels within a region of interest and at no other locations. On the other hand, a collapse cone hardware implementation is typically calculated from a dose interaction point of view, in which the calculation is performed originating at every non-zero TERMA value. There are advantages to each different method of dose calculation. For the dose interaction point of view, it is possible to determine the effect of changed beams on the dose without recalculating the entire beam. The dose deposition point of view is usually more efficient if only a few voxels are required, but is at a disadvantage for a large number of voxels due to additional information that must be pre-calculated and stored. Because of these algorithm differences, the hardware and software versions of the collapse cone algorithm are compared and the reasons for the speedup of the hardware version are analyzed.

The maximum sustained floating point performance for both the hardware implementation and the CPU shows that some advantages are gained. The maximum floating point performance in MFLOPS for an INTEL® PENTIUM M® 1.6 GHz is 694.9. This was obtained by performing a matrix multiply that fit entirely in the cache of the processor. Calculations done for the hardware implementation show that it is capable of running at approximately 5600 MFLOPS. The number of floating point units of different types present in the hardware implementation are shown in Table 18.

TABLE 18

Number and Type of Floating Point Units in Collapse Cone HW Implementation

| Unit Type | # Present |
|---|---|
| Multiply | 45 |
| Add | 36 |
| Subtract | 17 |
| Divide | 13 |
| Sqrt | 1 |

The number of MFLOPS was obtained by assuming that each floating point unit ran at 50 MHz and the knowledge that each unit is completely pipelined. If NumFP stands for the number of floating point units present and f represents the frequency they are running at, then total FLOPS is NumFP*f. Dividing the result by $10^6$ yields MFLOPS. The difference in MFLOPS between the hardware and software implementations leads to a factor of 8 increase in the number of floating point operations which can be performed.

FPGAs exhibit speed advantages over CPUs in more ways than simply performing calculations in parallel, such as by controlling software instruction mix. For example, using the Pin binary instrumentation tool provided by INTEL®, the dynamic instruction counts of the software program were obtained. These instructions were then divided into 4 different categories, integer arithmetic, memory operations, floating point arithmetic, and control instructions. The breakdown of the percentages of total instructions executed by category includes 12.1% for integer arithmetic (IntOps), 46.0% for memory operations (MemOps), 26.6% for floating point arithmetic (FPOps), and 15.3% for control operations (ControlOps). The total number of dynamically executed instructions was 94,024,735,126 with 384 cones.

In view of the mix of instructions with the hardware implementation, neither the memory operations nor the control instructions are of particular significance. The memory operations can be ignored because they are overshadowed by computation. In a normal CPU, memory locations must be loaded before they can be used, but in this implementation, memory is loaded in parallel with computation, so while loads and stores do take place, they do not add to the overall computation time. If needed, these instructions can typically be shadowed by the parallel computation being done. If those are eliminated, then only 38.7% of the original instructions remain. If it is assumed that the integer operations can be run with the same increase in performance as the floating point operations (a factor of 8), then the overall speedup of the hardware over the software would be approximately 20.7×, as shown in Equation 33. Table 17 shows an overall speedup of between 23.51× and 24.95×. The 20.7× speedup is a reasonable estimation of the overall speedup.

$$\text{Time} = 1/(OrigComputationTime* \\ (100\% - MemOps - ControlOps)/8) \\ = 1/(1*(38.7\%)/8) \\ = 20.7.$$

Equation 33

Multi-Level Parallel Dose Calculation

As described above, calculation of radiation dose may also employ a two level parallel structure to implement the collapsed cone algorithm. At a higher of two levels multiple direction modules provide the ability of depositing energy for different directions in parallel. At the lower level, multiple dose deposition engines can be employed to simultaneously compute the energy deposition by multiple radiation rays. In other words, each deposition engine may operate in parallel with one or more other deposition engines, thereby relieving each deposition engine of any co-dependency. Moreover, ray-tracing and energy calculation are separated into independent hardware modules so that data from ray-tracing can be fully reused. These unique design choices lead to a nearly linear speedup. Moreover, the multi-engine architecture is able to alleviate the demand on the computation time due to larger input sizes. The proposed architecture described below can also readily benefit from the computational power provided by multi-FPGA systems.

The collapsed cone algorithm could be implemented either from the "interaction point of view" or "deposition point of view." With the former, energy released from every interaction point in the irradiated volume is computed according to the distribution implied by the kernel. This means that the dose distribution is recalculated for the entire volume, even when the dose distribution for only a few numbers of voxels is of interest. Similar to many treatment planning systems (TPSs), we adopt the deposition point of view for efficiency.

From the deposition point of view, the final dose of a voxel $(v_x, v_y, v_z)$ is the sum of the partial dose from all the transport lines passing through $(v_x, v_y, v_z)$. To ease the hardware design, we elect to use the Cartesian coordinates to perform dose calculation. Let $(s_i, S_j, s_k)$ be the originating point of a transport line passing through $(v_x, v_y, v_z)$, and m, n be the zenith angle index and azimuth angle index, respectively. Equation 34 summarizes the computation for $(v_x, v_y, v_z)$.

$$D(v_x, v_y, v_z) = \sum_m \sum_n s_i, s_j, s_k \sum_{\in seedplane} D_{mn}^{(x,y,z)}(s_i, s_j, s_k).$$

Equation 34

In Equation 34, $D_{mn}^{(x,y,z)}$ is $D_{mn}(r_i)$ expressed in Cartesian coordinates. One feature of Equations 34, 11, and 12 is that data dependencies are limited, thus certain operations may be performed in parallel. In particular, a two-level parallel architecture may accomplish the computation of $D_{mn}^{(x,y,z)}$. At a lower level of the example two-level architecture, for given $(s_i, s_j, s_k)$, m and n values, the partial dose in $(v_x, v_y, v_z)$ contributed by all the voxels along the transport line is accumulated in parallel according to Equations 11 and 12. Note that for a given direction $\Omega_{mn}$, the voxels along the transport line only share the TERMA, ρ and η values. At a higher level of the example two-level architecture, multiple transport lines (corresponding to the last summation in Equation 34) can be considered in parallel. This two-level parallel architecture leads to a signification acceleration of the dose calculation process.

Figure 27:
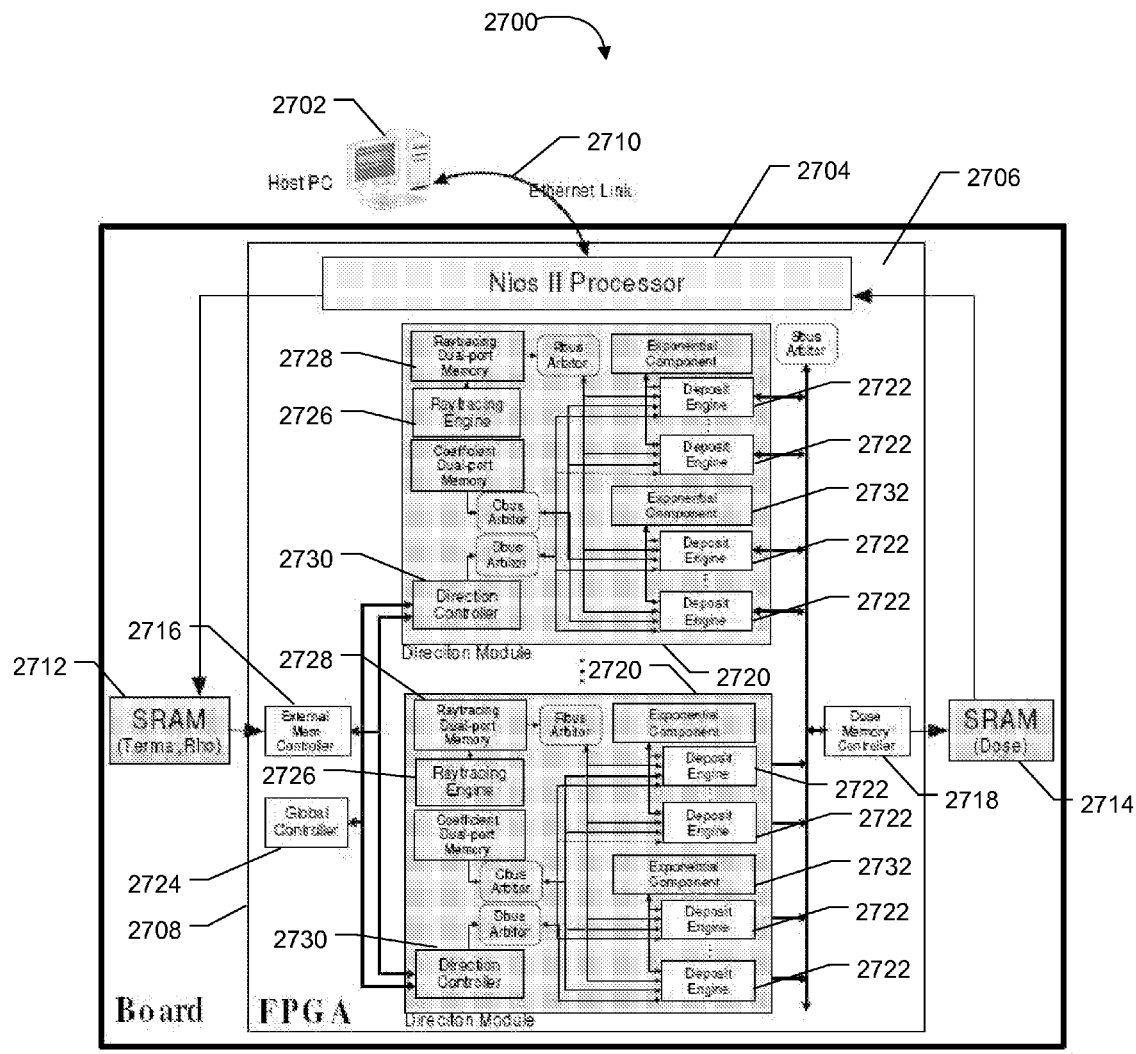
FIG. 27 is a block diagram of an example two-level parallel architecture system.

The overall structure of the example dose calculation system is shown in FIG. 27. The example system 2700 includes a host PC 2702, a NIOS II® processor 2704, and dedicated hardware 2706 for dose calculation, with the latter two being implemented on an FPGA chip 2708. The PC 2702 is responsible for handling a user interface and providing certain software based computation. The NIOS II® processor 2704 functions as a controller for managing the communication between the host PC 2702 and the dedicated hardware 2706. Communication may be achieved through an Ethernet link 2710.

From a data-flow point of view, implementing the collapsed-cone algorithm on an FPGA may be seen as designing a computation accelerator for the host PC 2702. Deciding what computations should be executed on the PC 2702 and on the hardware 2706 contributes to the overall system 2700 performance. Certain functions in the dose calculation, such as calculating TERMA, may not be time-consuming even when realized in software. The parameters ρ and η used in Equations 11 and 12 may also be derived from CT images without incurring significant computational overhead. Therefore, these functions may be executed on the host PC 2702.

In the illustrated example of FIG. 27 minimal computation is needed from the NIOS II® processor 2704. The processor is only responsible for the communication between the host PC 2702 and the FPGA board 2708. After receiving TERMA, ρ, and η through the Ethernet 2710, the NIOS II® processor 2704 writes such data into on-board SRAM 2712. After the dedicated hardware 2706 completes the dose calculation, the NIOS II® processor 2704 may send the dose results stored in SRAM 2714 (shown on the right of the FPGA chip) back to the host PC 2702. An external memory controller 2716 and a dose memory controller 2718 may be used to access the necessary information (ρ, η, TERMA, and dose) stored in the two SRAMs 2712 and 2714.

In the illustrated example of FIG. 27, the dedicated hardware 2706 includes multiple direction modules (DMs) 2720 as well as several miscellaneous controllers. Inside each DM 2720, there are multiple deposit engines (DEs) 2722 and other auxiliary components. Each DE 2722 may be responsible for the calculation of $D_{mn}^{(x,y,z)}(s_i, s_j, s_k)$, and each DM 2720 is designed to calculate $\Sigma_{(i,j,k) \in seedplane} D_{mn}^{(x,y,z)}(s_i, s_j, s_k)$, thus realizing the two-level parallel architecture discussed above.

After each DM 2720 is initialized to start a new direction by the Global Controller 2724, a ray-tracing engine (RE) 2726 may generate the seed plane and perform reference ray-tracing. The segment length Δr and the next voxel coordinates may be stored into a ray-tracing dual-port memory 2728 for future use by the DEs 2722 in the DM 2720. Once the seed plane is generated, a direction controller 2730 may produce corresponding transport lines and send them to available DES 2722 one by one. The receiving DEs 2722 may then start to calculate the dose according to Equations 11 and 12. Finally, in the illustrated example, the dose results are accumulated and stored in the external SRAM 2714 by the dose memory controller 2718. Persons having ordinary skill in the art will appreciate that multiple 32-bit on-chip buses (Rbus, Cbus, Dbus, Sbus) are implemented to connect different components by exploiting the rich routing resource(s) on FPGA chips. For simplicity, a daisy chain is adopted to handle simultaneous bus-access demands.

Due to resource limitations that may be encountered, which typically depend on available hardware resources, adjustments to the design structure may be appropriate. Table 19 summarizes example logic usage on, for example, a STRATIX II® 2S180 for different floating-point functions and the DE 2722.

TABLE 19

Logic Usage of Different Functions

| Function | LE | DSP | Memory |
|---|---|---|---|
| Exponential | 2762 | 0 | 1503 |
| Divider | 1632 | 0 | 123 |
| Multiplier | 344 | 7 | 0 |
| Adder | 688 | 0 | 0 |
| DE | 2401 | 0 | 0 |

As shown in Table 19, the floating-point exponential function (exponential component 2732 in FIG. 27) has a relatively high logic usage. As a result, several DEs 2722 may share the same exponential component 2732. As a rough estimate, STRATIX II® 2S180 is capable of holding approximately 40 DEs 2722.

Ray Tracing

Figure 28:
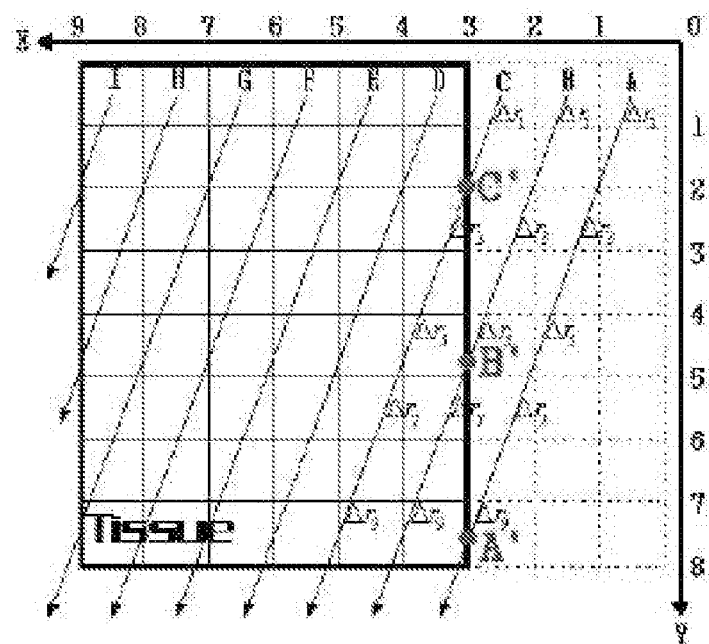
FIG. 28 is an example plot of two dimensional ray-tracing.

Ray-tracing is typically on the critical path of computing $D_{mn}^{(x,y,z)}(s_i, s_j, s_k)$ in each DE 2722. Note that $D_{mn}^{(x,y,z)}(s_i, s_j, s_k)$ in Equation 34 is a function of Δr. Rather than calculate Δr for every dose, this computation requirement may be greatly reduced by utilizing the seed plane and transport line concepts described above. A simplified 2-dimension example, as shown in FIG. 28, is used to explain this approach. Here, the tissue volume is defined by the area {Tissue|3<x<9, 0<y<8}. The seed plane then regresses to line y=1. In the illustrated example of FIG. 28, there are a total of 9 transport lines marked as A-I, respectively.

Transport lines that may partially fall outside the boundary of the tissue volume must be handled, such as example transport lines A-C in FIG. 28. An example manner of addressing the out-of-boundary issue includes calculating the points at the intersections of the tissue boundary and the transport lines, e.g., {A', B', C'}, and then computing the dose deposited in the voxels starting from {A', B', C'}. As a result, unnecessary computations for the area(s) outside the tissue are eliminated. However, the method requires that ray-tracing for these transport lines be performed separately. Hence separate ray-tracing is performed by each individual DE 2722, which may be very costly in terms of logic element usage.

Due to the symmetry and parallelism in the voxels under consideration for a group of parallel transport lines, the segment length Δr repeats for the parallel transport lines. To exploit this feature, virtual voxels may be padded (shown as dashed lines in FIG. 28) within the seed plane boundary. The TERMA, ρ and η values for these padded voxels are all assumed to be zero. It follows then that each DE 2722 may start "ray-tracing" from the voxel residing at the seed plane. The segment length Δr and the coordinates of the next voxel that the transport line is going to enter may be calculated by the RE 2726 and stored in the ray-tracing dual-port memory 2728. In the illustrated example, each DE addresses the memory in sequence to get the ray-trace information step by step.

The above design approach also provides the opportunity for the ray-tracing and the partial dose calculation to be performed in parallel. As ray-tracing proceeds, the example RE 2726 updates valid addresses to indicate the voxel on which the example RE 2726 is working. The address(es) issued by the DE 2722 may then be compared with this valid address. If the issued address is less than the valid address, it only costs one clock cycle to retrieve the ray trace information (e.g., by reading the ray-tracing dual-port memory 2728). Otherwise, the example DE 2722 may wait until the address becomes valid. Because the number of transport lines is usually relatively large, only the first several DEs need to wait for the ray-tracing information. This initialization cost is amortized among the following ray-tracing steps for the current direction. As a result, the average access time may be quite small.

System Memory

Embedded systems tend to have limited storage space in order to maintain lower cost. Thus, efforts may be employed to optimize the memory usage according to the application and the features provided by the hardware platform. Care should be taken when allocating data between on-chip and on-board memory components. Memory requirements for the dose calculation process may come from several areas. In general, the dose for a given voxel may be expressed by Equation 35.

$$D_{ri} = f(D_{ri-1}, T, \rho, \Theta, \Omega_{mn}, A_m, a_m, B_m, b_m, \Delta r).$$  Equation 35

In Equation 35, $D_{ri-1}$ is the dose contribution from previous voxels along the line of the ray-trace. One 32-bit register is sufficient to store $D_{ri-1}$ because the DE 2722 calculates the dose along each transport line iteratively. The sizes of TERMA, ρ, and η depend on the size of the matrix used to represent the voxels in the tissue volume and can be rather large. Therefore, they may be stored in the external off-chip memory. In the illustrated example, for a 100×100×100 voxel matrix, each variable needs approximately 32 Mbits of storage space (stored in the 32-bit floating point format).

The coefficients $A_m$, $a_m$, $B_m$, and $b_m$ in Equation 35 are all related to the zenith angles of the cone directions. As number of cones increases, the precision of the dose results increase. Typically, the number of cones is less than 500. The example implementation described herein uses, for example, 384 directions (48 zenith angles and 8 azimuth angles). Accordingly, these coefficients only need about 6 Kbits of memory, which may be stored in the on-chip memory without significantly increasing the overall memory requirement.

The value $\Omega_{mn}$ is a constant for a given direction, which may be calculated and/or tabulated. For example, tabulation may be employed to lower the logic resource usage. Moreover, to avoid evaluating trigonometric functions with logic resources, 384 direction cosines may also be stored in the on-chip memory, which would require approximately 50 Kbits of memory.

As discussed above, $\Delta r$ is the physical distance that the transport line traveled within the voxel. For each ray-tracing step, $\Delta r$ and the coordinates of the next voxel are stored in the memory, which results in approximately 128 bits for every step. To estimate the total memory requirement by the ray-tracing process includes determining how many segments the longest transport line is divided into during the whole calculation process (i.e., the maximum number of ray-tracing steps).

As shown in FIG. 8, the longest transport line is the diagonal of a box with edges $$\left|\frac{h'd_x}{\max(d_x, d_y, d_z)}\right|, \left|\frac{h'd_y}{\max(d_x, d_y, d_z)}\right|, \text{ and } \left|\frac{h'd_z}{\max(d_x, d_y, d_z)}\right|,$$

where h' is tissue length along the direction with the maxim absolute value. The maximum ray-trace segments for direction K, whose direction cosine is denoted by $\{d_x, d_y, d_z\}$, is then given Equation 36.

$$S_K = \left\lceil \left|\frac{h'd_x}{\max(d_x, d_y, d_z)L_x}\right| \right\rceil + \left\lceil \left|\frac{h'd_y}{\max(d_x, d_y, d_z)L_y}\right| \right\rceil + \left\lceil \left|\frac{h'd_z}{\max(d_x, d_y, d_z)L_z}\right| \right\rceil. \quad \text{Equation 36}$$

In Equation 36, $(L_x, L_y, L_z)$ is the size of the unit voxel. The capacity of the on-chip ray-tracing dual-port memory 2728 in each DM 2720 is then determined by Equation 37.

$$C_{raytrace} = 128 \max(S_1, S_2, \ldots, S_M)(\text{bit}). \quad \text{Equation 37}$$

In Equation 37, M is the total number of zenith angles.

To improve the performance of the memory subsystem, several example mechanisms have been introduced in the hardware design. First, for each DE, shadow registers may be employed to pre-fetch necessary information for the next ray-tracing step, which then allows certain memory access to overlap with the calculation. Second, a simple cache may be implemented in the external memory controller to reduce the read access time of the off-chip memory. Similarly, while writing the final dose in the dose memory, a write buffer and a 4-stage accumulation pipeline is designed in the dose memory controller to fully utilize the bandwidth of the dose memory.

Parallel Structure Implementation

In the illustrated example two-level parallel structure described herein, implementation was designed on an Altera DSP development board, which contains a STRATIX II® EP25180 FPGA and 1 MB SRAM (10 ns speed grade). Persons having ordinary skill in the art will appreciate that other equipment may be employed. Several electronic design automation (EDA) tools were used during the design process, which include QUARTUS II®, SYNPLIFY PRO® and ModelSim®. The design was mainly developed in VERILOG®. After compilation, the design with one DE may run at 117.2 MHz. The clock frequency is mainly restricted by the performance of the floating-point units. For simplicity, 100 Mhz is used as the hardware working frequency.

To compare with the software implementation option, the collapsed cone algorithm as used in the hardware design was also implemented in the C language. The performance result of the software was obtained for a PC with 2.4 GHz CPU and 512 MB of memory. To test the implementations, a realistic radiation treatment plan was adopted, in which the voxel size was 1 cm×1 cm×1 cm, and a phantom of size 30 cm×30 cm×30 cm (about the size of the human neck area) was used. The irradiated field was 20 cm×20 cm, and the source-to-skin distance was 100 cm. The resultant input data sizes (for TERMA, $\rho, \eta$, etc.) may readily fit in the on-board memory of the DSP development board.

Table look-ups were employed in the dose calculation instead of evaluating Equations 10 and 11. This approach reduces the computation time significantly, while most of the CPU time is spent on the ray-tracing task(s). For comparison purposes, the table-look-up operation is simulated by replacing DE with a simple logic (i.e., a fake DE), which simply holds for 3 clock cycles to simulate the table look-up operation in calculating dose. Additionally, a problem scale of 16×16×64 was chosen, which is similar to the matrix size of 30×30×30. The computing platform used in the comparison was a PC with CPU speed of 866 Mhz. To be fair, the computation time on the PC was increased by three times to account for the difference in the CPU frequencies.

Table 20 compares the execution time for hardware and software when tabulated kernel and analytical kernel is adopted separately.

TABLE 20

| Comparison of Execution Time | | |
|---|---|---|
| Kernel | Implementation | Time(s) |
| Tabulated Kernel | Software | 0.333 |
| Tabulated Kernel | HW with 1 fake DE | 0.0673 |
| Analytical Kernel | Software | 6.1 |
| Analytical Kernel | HW with 1 fake DE | 5.674 |

When the tabulated kernel is used, the hardware is much faster than the software due to the pipelined design of the RE. When the analytical kernel is accepted, the running time for the HW is only slightly less than that of the SW due to the cost of bus access and the stall of the pipeline (the floating-point multiplier and exponential function used, which are the most important operators in DE, do not support pipelining).

Although the design with one DE may not lead to significant speedups compared with the software implementation, the power of the hardware architecture lies in the fact that multiple DEs may be included in a single implementation. By executing these DEs in parallel, greater speedups may be obtained. In Table 21, a summary of five hardware implementations is shown that contain different numbers of DEs. In these implementations, each DE has one independent exponential component.

TABLE 21

| Hardware Cost and Performance for Multiple DEs | | | | | |
|---|---|---|---|---|---|
| DE | Freq. (MHz) | ALUTs | Mem (Kbits) | Time (s) | speedup |
| 1 | 117.2 | 10973 | 2,767 | 5.674 | 1 |
| 2 | 112.8 | 14144 | 2,803 | 2.937 | 1.932 |
| 4 | 106.1 | 20616 | 2,887 | 1.525 | 3.720 |

TABLE 21-continued

Hardware Cost and Performance for Multiple DEs

| DE | Freq. (MHz) | ALUTs | Mem (Kbits) | Time (s) | speedup |
|----|-------------|-------|-------------|----------|---------|
| 8  | 99.3        | 33481 | 2,958       | 0.769    | 7.378   |
| 12 | 93.4        | 45985 | 3,179       | 0.615    | 9.226   |

From Table 21, it may be seen that the hardware cost (Col. 3 and 4) increases and the clock frequency (Col. 2) decreases, but the changes are relatively small with respect to the original values for a single DE. A decrease in the clock frequency is attributed to the increasing pressure of placing and routing larger designs. The total dose calculation time (Col. 5) decreases almost linearly, except the 12 DE case. Accordingly, the speedup (Col. 6) achievable by the architecture increases proportionally with the number of Des, but may slows down gradually because of the impact of accessing shared information. For the given FPGA board, when the number of DEs is greater than 12, performance saturates because the bandwidth of the external memory becomes the bottleneck of the system. That is, there are always some DEs waiting for memory operations. However, persons having ordinary skill in the art will appreciate that other FPGAs may not exhibit similar performance issues, thereby allowing greater than 12 DEs to be employed to improve performance.

Additionally, to alleviate the memory bottleneck, the memory bandwidth could be increased by expanding data bus width, or more efficient memory subsystems may be employed/designed. At least one straightforward approach may include duplicating the TERMA, $\rho$ and $\eta$ information into several separate memory chips. Each chip may supply (as input for K) direction modules. The dose results of these K direction modules may then be added up and saved into separate memory chips. This architecture may be able to extended into multi-FPGA systems and/or bring even greater speedup for dose calculation objectives. When the matrix size increases, this feature would still be able to keep relatively low computation times by deploying additional DEs, as needed.

Although the teachings of the invention have been illustrated in connection with certain embodiments, there is no intent to limit the invention to such embodiments. On the contrary, the intention of this application is to cover all modifications and embodiments fairly falling within the scope of the appended claims either literally or under the doctrine of equivalents.

What is claimed is:

1. A method for calculating radiation dose comprising:
   receiving a tissue matrix, the tissue matrix comprising a plurality of voxels;
   producing a first plurality of transport lines with a direction controller, each transport line indicative of a cone of irradiated energy;
   receiving each of the produced first plurality of transport lines in an available one of a plurality of deposit engines;
   calculating at least one radiation dose with the plurality of deposit engines receiving the first plurality of transport lines substantially in parallel with producing a second plurality of transport lines with the direction controller.

2. A method as defined in claim 1, wherein calculating the at least one radiation dose further comprises calculating a first dose with a first deposit engine and calculating a second dose with a second deposit engine.

3. A method as defined in claim 1, further comprising:
   providing the first and second plurality of transport lines from the direction controller to a plurality of deposit engines, and
   independently calculating a radiation dose associated with each of the first and second transport lines via the deposit engines.

4. A method as defined in claim 1, further comprising calculating a physical path length of the irradiated energy, the physical path length provided to the at least one deposit engine to calculate the at least one radiation dose.

5. A method as defined in claim 4, further comprising calculating the physical path length via a trace engine independently of the at least one deposit engine.

6. A method as defined in claim 1, further comprising generating a first seed plane from a first portion of the tissue matrix and a second seed plane from a second portion of the tissue matrix, the at least one radiation dose independently calculated by the at least one deposit engine.

7. A method as defined in claim 1, further comprising employing a collapsed cone algorithm to calculate the at least one radiation dose.

8. A method as defined in claim 1, wherein the step of calculating a radiation dose further comprises:
   receiving via a computer-readable memory first information indicative of a patient anatomy;
   receiving via the computer-readable memory second information indicative of a radiation beam parameter;
   formatting the first and second information as a hardware-readable data structure; and
   executing a dose calculation algorithm on a hardware-based calculation engine programmed to read the hardware-readable data structure and to execute computer-readable instructions to calculate the radiation dose from the formatted data structure.

9. A method as defined in claim 8, wherein the hardware-based calculation engine is a field programmable gate array (FPGA).

10. A method as defined in claim 9, further comprising calculating a kernel associated with a radiation beam.

11. A method as defined in claim 8, further comprising configuring the dose calculation algorithm to execute with at least two parallel threads.

12. A method as defined in claim 11, further comprising independently executing the at least two parallel threads.

13. A method as defined in claim 8, further comprising allocating a plurality of memory segments accessible by the hardware-based calculation engine, each of the plurality of memory segments associated with at least one of a plurality of dose calculation threads.

14. A method as defined in claim 13, further comprising independently accessing each of the plurality of memory segments by a field programmable gate array (FPGA).

15. A method as defined in claim 14, further comprising processing at least one of the plurality of dose calculation threads by the FPGA comprising at least one direction module.

16. A method as defined in claim 8, wherein the dose calculation algorithm comprises at least one of a collapsed cone algorithm or a Monte-Carlo algorithm.

17. A method as defined in claim 8, further comprising providing the hardware-based calculation engine with a plurality of physical path lengths of irradiated energy through the patient anatomy.

18. A method as defined in claim 17, further comprising recursively calculating the plurality of physical path lengths with a ray tracing engine.

19. A method as defined in claim 18, further comprising independently calculating the plurality of physical path lengths via a plurality of ray tracing engines.

20. A method as defined in claim 18, further comprising independently calculating the plurality of partial dose in at least one voxel via a plurality of deposition engines.

21. A method as defined in claim 8, wherein the hardware-readable data structure comprises a matrix of tissue densities associated with the patient anatomy.

22. A method as defined in claim 8, further comprising computing raytrace information, the raytrace information stored in a memory block.

23. A method as defined in claim 22, further comprising sharing the raytrace information by a plurality of deposition engines.

24. A method as defined in claim 8, further comprising calculating dose along a plurality of kernels among a plurality of hardware blocks.

25. A method as defined in claim 24, further comprising independently calculating the radiation dose among the plurality of hardware blocks.

26. A method as defined in claim 24, further comprising calculating via the plurality of hardware blocks in parallel.

27. A method as defined in claim 8, further comprising controlling a plurality of deposition engines by a direction controller.

28. A method as defined in claim 8, wherein formatting the at least one of first or second information comprises a three-dimensional matrix to represent an electron density of the patient anatomy.

29. A method as defined in claim 8, wherein the hardware-readable data structure comprises a three-dimensional matrix indicative of radiation beam characteristics.

30. A method as defined in claim 29, wherein the radiation beam characteristics comprise at least one of a polyenergetic beam energy distribution or a monoenergetic beam energy distribution.

31. A method as defined in claim 30, wherein the at least one of the polyenergetic beam or the monoenergetic beam comprises a single point or a narrow beam.

32. A method as defined in claim 8, wherein the hardware-readable data structure further comprises an accumulation dose matrix.

33. A method as defined in claim 8, further comprising generating a first seed plane from a first portion of a tissue matrix and a second seed plane from a second portion of the tissue matrix.

34. A method as defined in claim 33, further comprising invoking a collapsed cone convolution/superposition algorithm with the first and second seed planes.

35. A method as defined in claim 1, wherein the step of calculating the at least one radiation dose further comprises:
    receiving by a processor an indication of total energy per unit mass (TERMA) associated with an interaction point;
    determining by the processor whether at least one voxel includes a non-zero TERMA; and
    ray-tracing by the processor the at least one voxel when the at least one voxel includes the non-zero TERMA.

36. A method as defined in claim 35, wherein ray-tracing comprises at least one of an x-axis direction, a y-axis direction, or a z-axis direction.

37. A method as defined in claim 36, wherein the at least one of the x-axis direction, the y-axis direction, or the z-axis direction is stored in at least one of a plurality of memory blocks.

38. A method as defined in claim 37, further comprising accessing the at least one of the plurality of memory blocks in parallel.

39. A method as defined in claim 35, the method further comprising at least one of:
    calculating a distribution of primary energy particles via a primary energy calculator, or calculating a distribution of secondary energy particles via a scatter energy calculator; and
    calculating at least one of the distribution of primary energy particles via the primary energy calculator or the distribution of secondary energy particles via the scatter energy calculator.

40. An article of manufacture storing machine readable instructions which, when executed, cause a machine to:
    receive a tissue matrix, the tissue matrix comprising a plurality of voxels;
    produce a first plurality of transport lines with a direction controller, each transport line indicative of a cone of irradiated energy;
    transmit each of the produced first plurality of transport lines to an available one of a plurality of deposit engines; and
    calculate at least one radiation dose with the plurality of deposit engines substantially in parallel with producing a second plurality of transport lines with the direction controller.

41. An article of manufacture as defined in claim 40, wherein the machine readable instructions further cause the machine to calculate a first dose with a first deposit engine and calculate a second dose with a second deposit engine.

42. An article of manufacture as defined in claim 40, wherein the machine readable instructions further cause the machine to provide the first and second plurality of transport lines to a plurality of deposit engines, the deposit engines independently calculating a radiation dose associated with each of the first and second transport lines.

43. An article of manufacture as defined in claim 40, wherein the machine readable instructions further cause the machine to calculate a physical path length of the irradiated energy, the physical path length provided to the at least one deposit engine to calculate the at least one radiation dose.

44. An article of manufacture as defined in claim 43, wherein the machine readable instructions further cause the machine to calculate the physical path length independently of the at least one deposit engine.

45. An article of manufacture as defined in claim 40, wherein the machine readable instructions further cause the machine to generate a first seed plane from a first portion of the tissue matrix and a second seed plane from a second portion of the tissue matrix, the at least one radiation dose independently calculated by the at least one deposit engine.

46. An article of manufacture as defined in claim 40, wherein the machine readable instructions further cause the machine to calculate the at least one radiation dose with a collapsed cone algorithm.

47. An apparatus to calculate radiation dose comprising:
    a field programmable gate array (FPGA);
    at least one direction module programmed into the field programmable gate array, the at least one direction module comprising a direction controller to produce a plurality of transport lines, and a plurality of deposit engines to calculate radiation dose; and
    a direction module controller coupled to each of the at least one direction module to facilitate parallel execution of the at least one direction module.

48. An apparatus as defined in claim 47, further comprising a ray-tracing engine to calculate a physical path length of irradiated energy, the physical path length provided to the plurality of deposit engines to calculate radiation dose.

49. An apparatus as defined in claim 48, further comprising an engine arbitrator to facilitate parallel execution of the ray-tracing engine and the plurality of the deposit engines.

50. An apparatus as defined in claim 47, further comprising a first memory to provide matrix data to the FPGA, the matrix data indicative of an area of interest of patient tissue.

51. An apparatus as defined in claim 50, wherein the first memory comprises at least one of total energy released per mass, mass density, exponential kernel, or electron volume density.

52. An apparatus as defined in claim 50, further comprising a second memory to store a plurality of calculated radiation doses from the plurality of deposit engines.

53. An apparatus as defined in claim 47, further comprising a plurality of direction modules, the plurality of direction modules communicatively coupled to the at least one direction module.

* * * * *